(12) United States Patent
O'Dea et al.

(10) Patent No.: US 9,131,898 B2
(45) Date of Patent: Sep. 15, 2015

(54) CATHETER, A BALLOON CATHETER AND A METHOD AND APPARATUS FOR MONITORING THE TRANSVERSE CROSS-SECTION OF A STOMA

(75) Inventors: John O'Dea, Bearna (IE); Adrian McHugh, Kilcolgen (IE); Eoin Bambury, Navan (IE)

(73) Assignee: Flip Technologies Limited, Galway (IE)

( * ) Notice: Subject to any disclaimer, the term of this patent is extended or adjusted under 35 U.S.C. 154(b) by 295 days.

(21) Appl. No.: 13/255,195

(22) PCT Filed: Mar. 9, 2010

(86) PCT No.: PCT/IE2010/000011
§ 371 (c)(1),
(2), (4) Date: Oct. 20, 2011

(87) PCT Pub. No.: WO2010/103502
PCT Pub. Date: Sep. 16, 2010

(65) Prior Publication Data
US 2012/0035642 A1 Feb. 9, 2012

(30) Foreign Application Priority Data

Mar. 9, 2009 (IE) .................................. S2009/0184
Apr. 21, 2009 (IE) .................................. S2009/0310
Jun. 4, 2009 (IE) .................................. S2009/0441

(51) Int. Cl.
*A61M 29/00* (2006.01)
*A61B 5/00* (2006.01)
(Continued)

(52) U.S. Cl.
CPC .............. *A61B 5/6853* (2013.01); *A61B 5/1076* (2013.01); *A61B 5/42* (2013.01);
(Continued)

(58) Field of Classification Search
CPC ................... A61M 25/1018; A61M 25/10184; A61M 25/10187; A61M 2025/1093; A61M 25/10; A61M 2025/0002; A61M 2025/1088; A61M 2025/1086; A61M 2025/10187; A61F 5/003–5/0059; A61F 5/0013; A61F 2005/0016; A61F 2005/002; A61B 5/6853; A61B 5/42; A61B 5/1076
USPC ...................................................... 604/101.01
See application file for complete search history.

(56) References Cited

U.S. PATENT DOCUMENTS 5,275,169 A * 1/1994 Afromowitz et al. ......... 600/486
5,785,685 A * 7/1998 Kugler et al. .............. 604/99.03
(Continued)

FOREIGN PATENT DOCUMENTS

| WO | 2004/075928 A2 | 9/2004 |
| WO | 2006/102905 A1 | 10/2006 |
| WO | 2008/042347 A2 | 4/2008 |

OTHER PUBLICATIONS

International Search Report for PCT/IE2010/000011 dated Dec. 15, 2010.

*Primary Examiner* — Amy R Weisberg
(74) *Attorney, Agent, or Firm* — Sughrue Mion, PLLC

(57) ABSTRACT

A balloon catheter comprises a catheter and a balloon located on the distal end of the catheter. A pair of stimulating electrodes for receiving a constant current stimulating signal when the balloon is inflated with an electrically conductive medium and a plurality of sensing electrodes for producing voltage response signals are located on the catheter. The voltage response signals are indicative of the values of the transverse cross-sectional area of the balloon adjacent the sensing electrodes. A first lumen accommodates the inflating medium to and from the balloon, and a second lumen accommodates electrically conductive wires to the stimulating and sensing electrodes. A pressure sensing element is located in a protective housing in the second lumen, and communicates through a communicating opening in the protective housing and through a communicating port in the catheter with a hollow interior region of the balloon. The balloon catheter may also be provided with a guide wire engaging element for engaging a guide wire externally of the balloon catheter.

16 Claims, 15 Drawing Sheets

(51) Int. Cl.
*A61B 5/107* (2006.01)
*A61M 25/10* (2013.01)
*A61M 25/00* (2006.01)

(52) U.S. Cl.
CPC ........... *A61M 25/10* (2013.01); *A61M 25/1018* (2013.01); *A61M 2025/0002* (2013.01); *A61M 2025/1086* (2013.01); *A61M 2025/1088* (2013.01); *A61M 2025/1093* (2013.01)

(56) References Cited

U.S. PATENT DOCUMENTS

| | | | | |
|---|---|---|---|---|
| 5,902,248 | A * | 5/1999 | Millar et al. | 600/485 |
| 6,010,511 | A * | 1/2000 | Murphy | 606/108 |
| 6,102,922 | A * | 8/2000 | Jakobsson et al. | 606/157 |
| 6,254,569 | B1 * | 7/2001 | O'Donnell et al. | 604/97.03 |
| 6,394,986 | B1 * | 5/2002 | Millar | 604/264 |
| 6,616,597 | B2 * | 9/2003 | Schock et al. | 600/18 |
| 7,192,397 | B2 * | 3/2007 | Lewkowicz et al. | 600/160 |
| 7,454,244 | B2 * | 11/2008 | Kassab et al. | 600/547 |
| 7,818,053 | B2 * | 10/2010 | Kassab | 600/547 |
| 7,993,336 | B2 * | 8/2011 | Jackson et al. | 606/41 |
| 8,012,149 | B2 * | 9/2011 | Jackson et al. | 606/34 |
| 8,078,274 | B2 * | 12/2011 | Kassab | 600/547 |
| 8,082,032 | B2 * | 12/2011 | Kassab et al. | 600/547 |
| 8,406,867 | B2 * | 3/2013 | Kassab | 600/547 |
| 2008/0161730 | A1 * | 7/2008 | McMahon et al. | 600/593 |
| 2009/0062684 | A1 * | 3/2009 | Gregersen et al. | 600/547 |
| 2009/0247945 | A1 * | 10/2009 | Levit et al. | 604/103 |
| 2010/0094328 | A1 * | 4/2010 | O'dea et al. | 606/192 |
| 2010/0222786 | A1 * | 9/2010 | Kassab | 606/127 |
| 2010/0305479 | A1 * | 12/2010 | O'Dea | 600/587 |
| 2010/0312181 | A1 * | 12/2010 | O'Dea | 604/96.01 |
| 2012/0095334 | A1 * | 4/2012 | Forster et al. | 600/439 |
| 2012/0215166 | A1 * | 8/2012 | Barki | 604/103.07 |

* cited by examiner

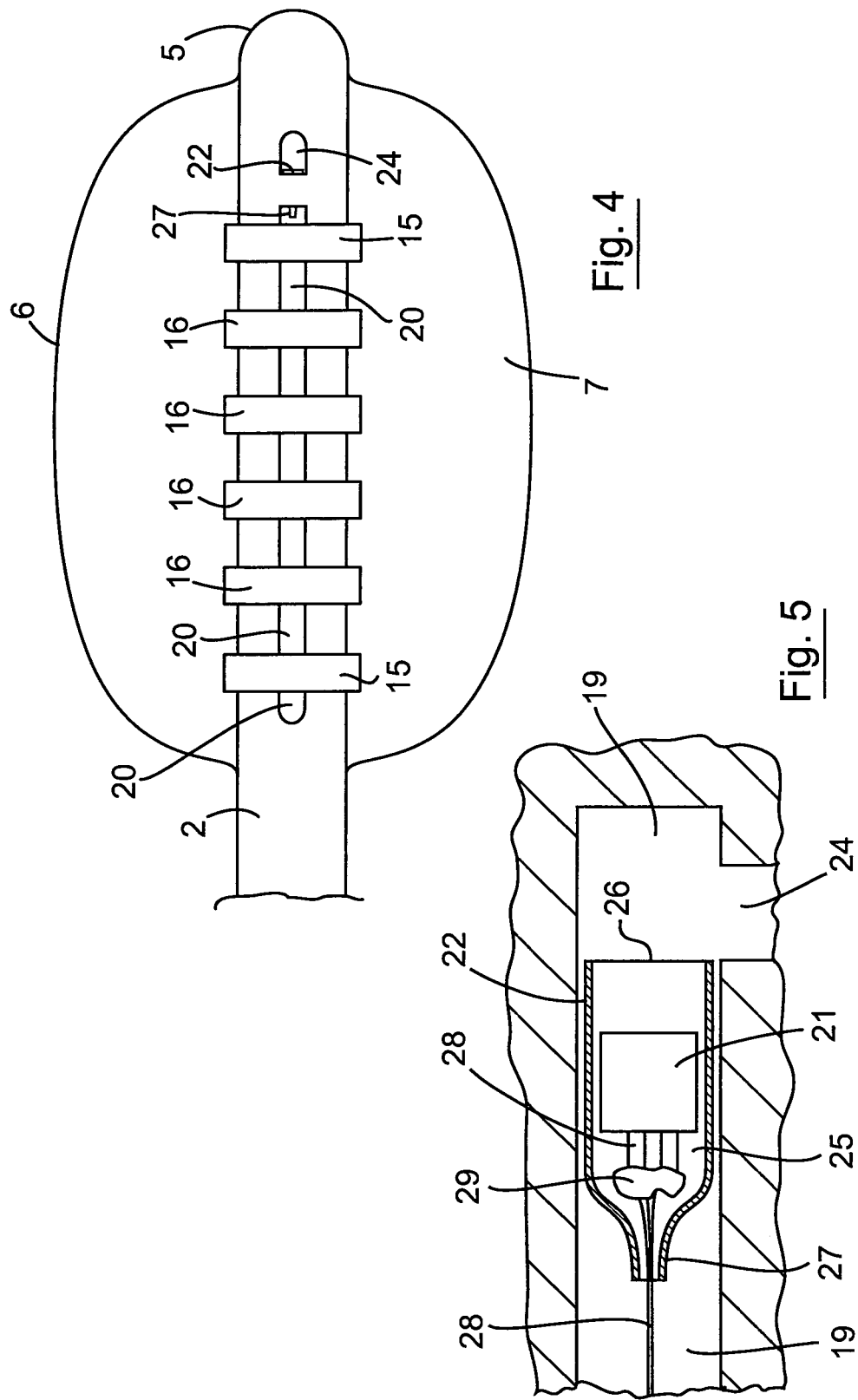

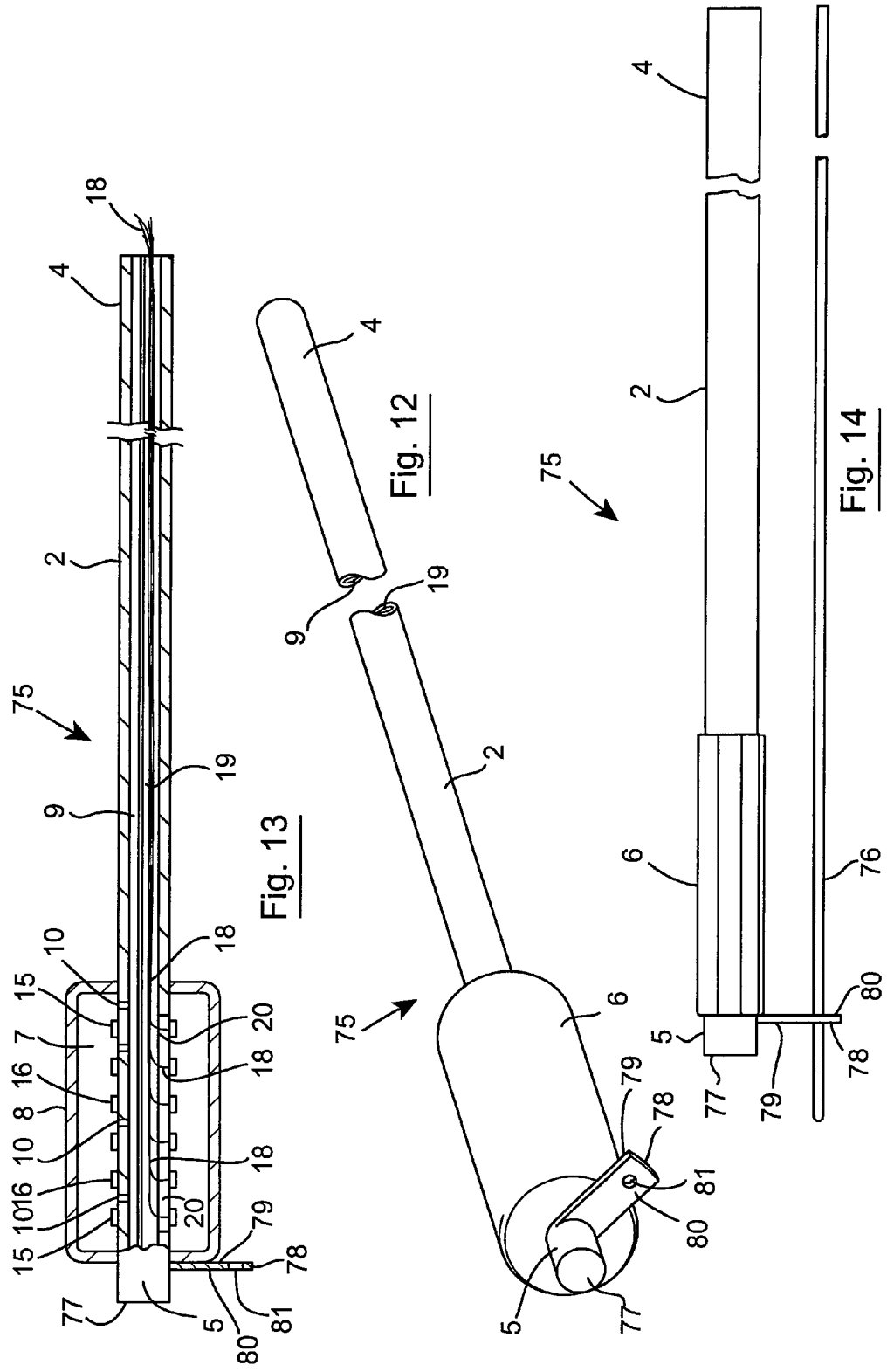

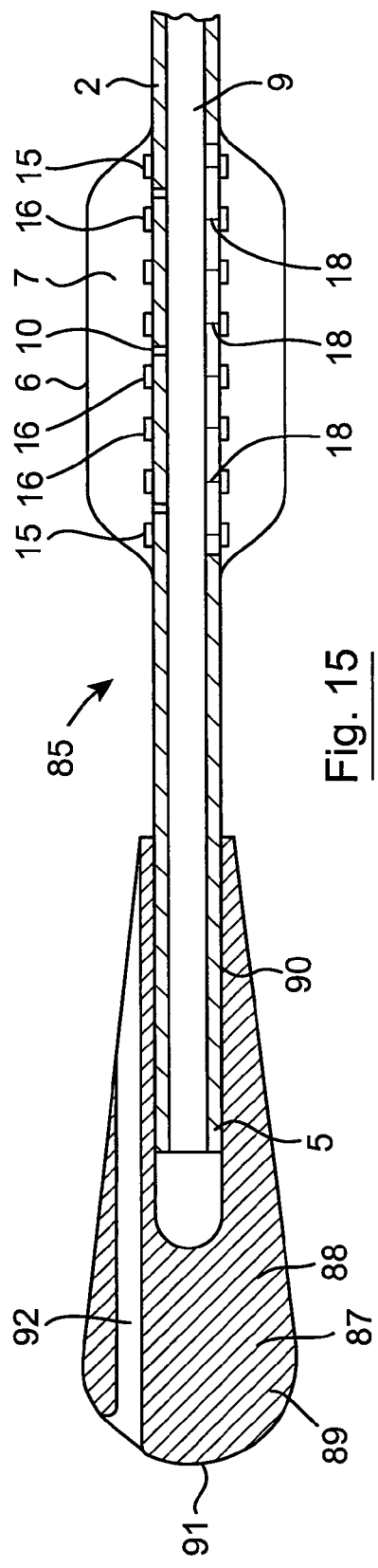
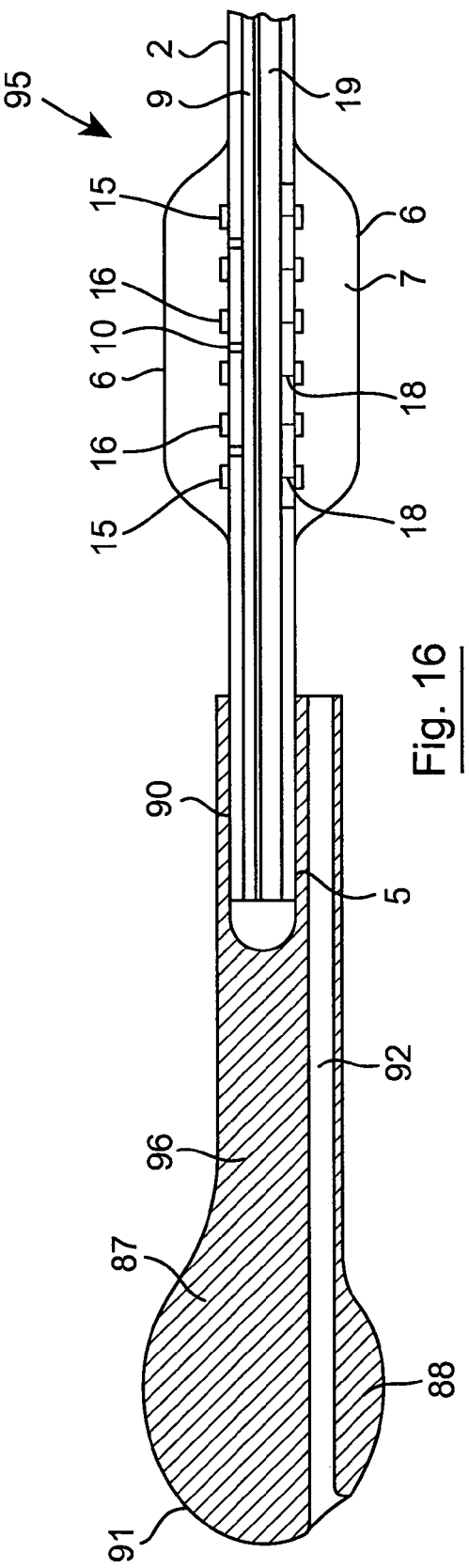
Fig. 15
Fig. 16

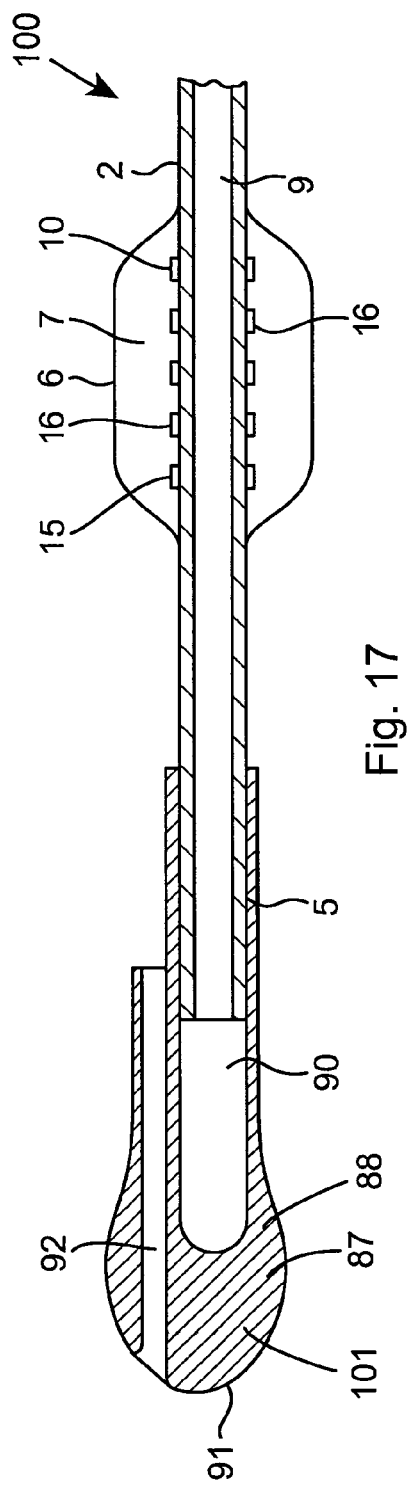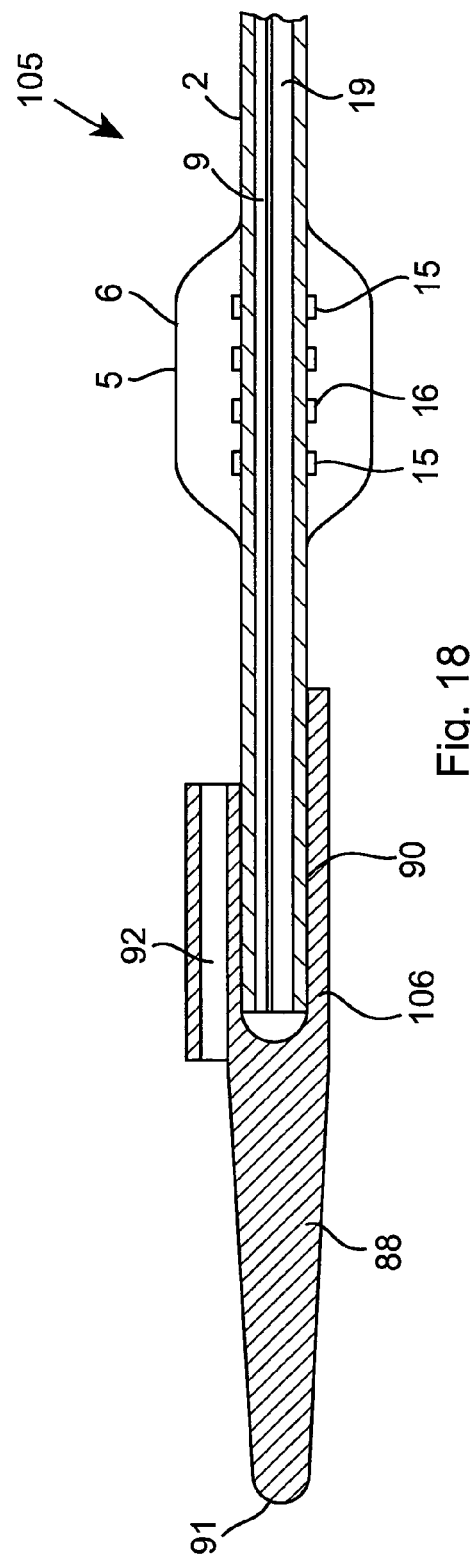

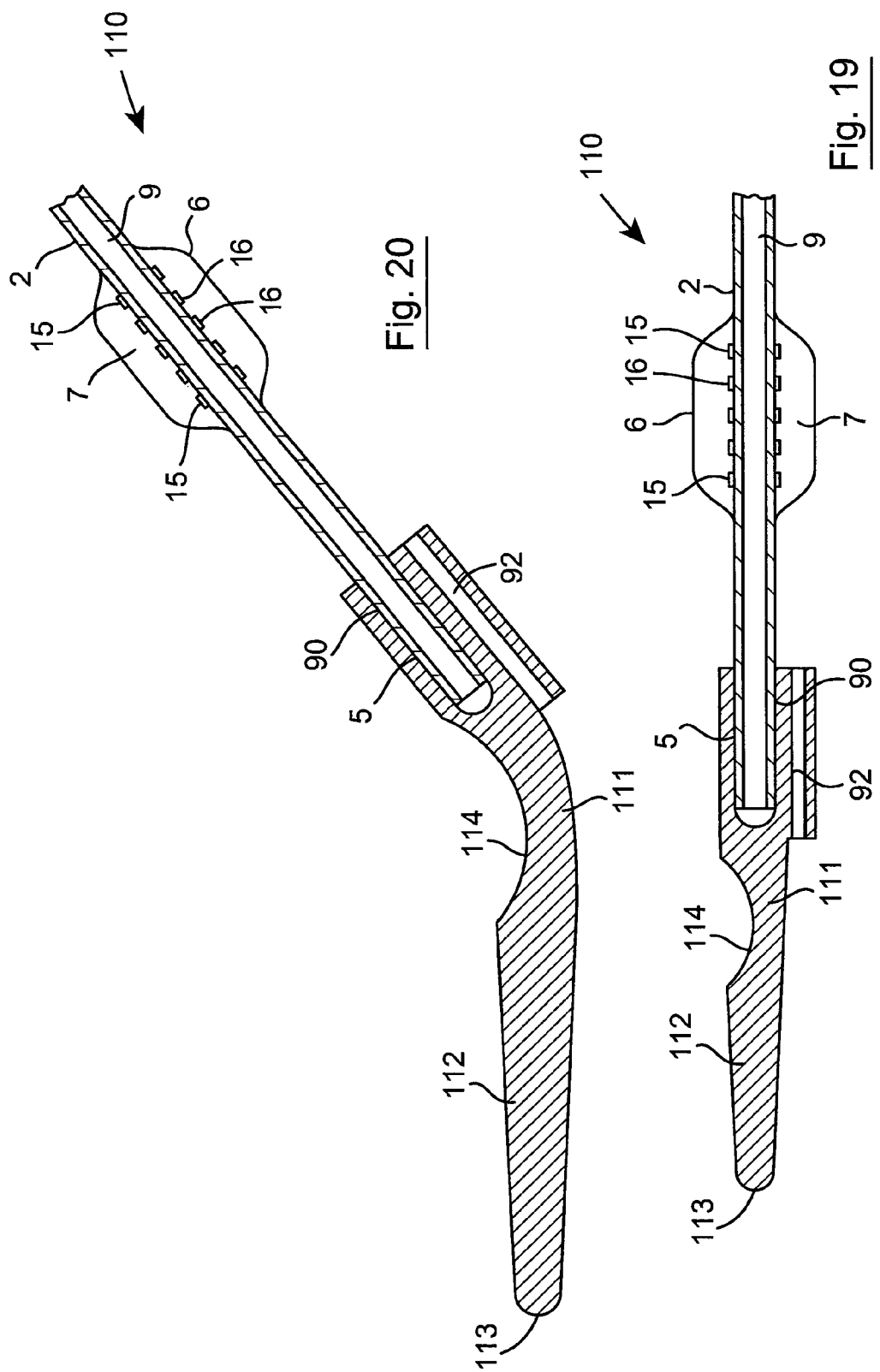

CATHETER, A BALLOON CATHETER AND A METHOD AND APPARATUS FOR MONITORING THE TRANSVERSE CROSS-SECTION OF A STOMA

CROSS-REFERENCE TO RELATED APPLICATIONS

The present application is a 35 U.S.C. §371 national stage entry of PCT/IE10/00011, which has an international filing date of Mar. 9, 2010 which claims priority to IRELAND S2009/0184 filed Mar. 9, 2009; IRELAND S2009/0310 filed Apr. 21, 2009; and IRELAND S2009/0441 filed Jun. 4, 2009.

BACKGROUND OF THE INVENTION

The present invention relates to a balloon catheter, and in particular, though not limited to a balloon catheter of the type for determining the volume and/or transverse cross-sectional diameter or area of a vessel, lumen, sphincter or stoma. The invention also relates to a catheter, and to a method and apparatus for monitoring the transverse cross-section of a stoma, and particularly for monitoring the transverse cross-section of a stoma during formation of the stoma, for example, during the formation of a stoma in a stomach. The invention also relates to a method for forming a stoma in a vessel.

Balloon catheters, in general, comprise an elongated catheter which extends between a proximal end and a distal end. An inflatable element, typically a balloon is located at the distal end of the catheter with the catheter extending through the inflatable element, so that the inflatable element defines with the catheter an annular hollow interior region extending around the catheter. A lumen extends through the catheter from the proximal end thereof to the inflatable element and communicates with the inflatable element for accommodating an inflating medium to and from the inflatable element for inflating and deflating the inflatable element. Measuring electrodes may be provided on the catheter for facilitating measuring of the transverse cross-sectional area and/or diameter and the volume of the inflatable element, and in turn, for measuring the transverse cross-sectional area and/or diameter and the volume of a lumen or vessel within which the inflatable element is located and inflated therein.

Such balloon catheters are used for carrying out an investigation or a procedure at a remote site in the human or animal body. For example, balloon catheters are used for determining the transverse cross-sectional area or diameter of a lumen or vessel, and are also used for determining the volume of all or a portion of a lumen or vessel. Such a lumen or vessel may, for example, be the oesophagus of a human or animal subject, a stomach or a part of a stomach, for example, a part of a stomach resulting from a bariatric procedure in a human or animal subject. Such balloon catheters are also used for determining the degree of relaxation of a sphincter, as well as the muscle tone of a sphincter, for example, the lower oesophageal sphincter of a subject. Needless to say, balloon catheters may be used for determining the transverse cross-sectional area, diameter and/or the volume of a lumen or vessel or a sphincter in any part of the gastrointestinal tract. Such balloon catheters are also used in the vascular and cardiovascular system of a human or animal subject for determining the transverse cross-sectional area and the volume of all or part of a vessel or lumen. Additionally, such balloon catheters are used for carrying out procedures at remote locations, for example, dilating an occlusion in a lumen or a vessel, and ablating tissue at a remote location in a lumen or a vessel.

However, in low pressure applications of such balloon catheters, in particular when a balloon catheter is used for determining the transverse cross-sectional area and/or the volume of a lumen, a vessel or a sphincter, it is essential to be able to accurately monitor the actual pressure within the inflatable element of an inflating medium which is used to inflate the inflatable element of the balloon catheter. This is particularly so when the inflatable element is being inflated to just fill the cross-section of the lumen or vessel, and when the pressure of the inflating medium is being monitored in order to determine when the inflatable element just fills the cross-section of the lumen or vessel. In general, known methods and systems for determining the pressure of the inflating medium in the inflatable element of a balloon catheter require monitoring the pressure of the inflating medium at the proximal end of the catheter. In other words, the pressure of the inflating medium is monitored at the location at which it is being delivered to the inflating medium accommodating lumen of the catheter. This is unsatisfactory due to the remoteness of the proximal end of the catheter from the inflatable element. By virtue of the fact that the proximal end of the catheter is remote from the inflatable element, in general, the pressure of the inflating medium read at the proximal end of the catheter does not accurately represent the pressure of the inflating medium in the inflatable element, due to the fact that a pressure drop occurs along the lumen between the proximal and distal ends thereof.

This is particularly so where the catheter of the balloon catheter is of relatively small transverse cross-sectional area in order to gain access through vessels and lumens of correspondingly small transverse cross-sectional area, in such catheters, the lumen which accommodates the inflating medium to the inflatable element is of proportionately small transverse cross-sectional area. The smaller the transverse cross-sectional area of the lumen through which the inflating medium is accommodated to and from the inflatable element, the greater is the pressure drop in the inflating medium accommodating lumen between the proximal end of the catheter and the inflatable element. Thus, in catheters of small transverse cross-sectional area a pressure reading taken of the inflating medium adjacent the proximal end of the inflating medium accommodating lumen does not accurately represent the pressure of the inflating medium in the inflatable element due to the pressure drop between the proximal end of the inflating medium accommodating lumen and the distal end thereof adjacent the inflatable element.

Furthermore, during inflating and deflating of the inflatable element, the pressure drop across the inflating medium accommodating lumen between the proximal end of the lumen and the distal end adjacent the inflatable element becomes significantly greater, and thus, a reading of the pressure of the inflating medium adjacent the proximal end of the inflating medium accommodating lumen would fail to produce an accurate indication of the pressure of the inflating medium within the inflatable element. Accordingly, there is a need for a balloon catheter which addresses this problem.

In such balloon catheters which comprise a plurality of axially spaced apart measuring electrodes located on the catheter within the inflatable element, the measuring electrodes, in general, are band type electrodes which extend around the catheter. In general, two of the measuring electrodes, namely, the two outermost electrodes are stimulating electrodes for receiving a constant current stimulating signal of known value. The remaining electrodes which are axially spaced apart from each other and are located between the stimulating electrodes and axially spaced apart from the stimulating electrodes are sensing electrodes. A constant current stimulating signal is applied to the stimulating electrodes when the inflatable element is inflated with an electrically conductive medium, such as a saline solution.

Response voltage signals produced on the respective sensing electrodes in response to the stimulating signal applied to the stimulating electrodes are indicative of the values of transverse cross-sectional area and diameter of the inflatable element adjacent the respective sensing electrodes. By processing such response voltage signals in suitable signal processing apparatus, the values of the transverse cross-sectional area and diameter of the inflatable element adjacent the respective sensing electrodes may be computed. Additionally, once the values of the transverse cross-sectional area of the balloon adjacent the respective sensing electrodes have been computed, by knowing the spacing between the respective sensing electrodes, the volume of the balloon can be computed, and the volume of a part of the balloon between any two sensing electrodes can also be computed.

However, a problem with such balloon catheters is that at locations along the inflatable element where the inflatable element is inflated to a relatively large diameter, the sensitivity with which the values of the transverse cross-sectional area of the inflatable element can be computed is relatively poor. Since the determination of the volume of the inflatable element between two selected sensing electrodes requires a determination of the values of the transverse cross-sectional area of the inflatable element adjacent the respective sensing electrodes which are located between the two selected sensing electrodes between which the volume is to be determined, if the values of the transverse cross-sectional area adjacent these sensing electrodes cannot be accurately determined, it will be impossible to accurately determine the volume of the relevant part of the inflatable element. The reason for the lack of sensitivity with which the values of the transverse cross-sectional area can be determined at relatively large diameters of the inflatable element is as a result of the relatively small voltage drop between adjacent ones of the sensing electrodes, due to the low impedance offered by the inflating medium between the adjacent ones of the sensing electrodes, which are adjacent locations where the transverse cross-sectional area of the inflated inflatable element is relatively large.

Therefore, in cases where a balloon catheter is required to determine the values of the transverse cross-sectional area of a vessel or lumen of varying transverse cross-sectional area, and in particular, where the transverse cross-sectional area varies significantly, in general, it is difficult if not impossible to accurately determine the values of the transverse cross-sectional area of the vessel at locations where the transverse cross-sectional area is relatively large by comparison to other locations of the vessel where the transverse cross-sectional area is relatively small. There is therefore a need for a balloon catheter which addresses this problem.

Catheters are used for accessing remote sites in a body of a human or animal subject such as a remote site in the oesophagus, stomach, and other organs and lumens of the digestive system. Typically, when used for accessing the oesophagus, stomach and small intestine, the catheter, in general, is inserted nasally or orally. When used to access a remote site in the large intestine, bowel and the like, the catheter is entered rectally. Catheters are also used for accessing a remote site in the arterial and venal vascular systems of the human or animal body, and also for accessing a remote site in the cardiovascular system of the human or animal body. However, in the arterial and venal vascular system and the cardiovascular system the catheter, in general, is guided to the remote site along a guide wire. The guide wire is initially passed through the vascular system to the remote site. The catheter is provided with an internal lumen for slideably engaging the guide wire. Once a distal end of the guide wire has accessed the remote site, the internal lumen of the catheter at the distal end thereof is engaged on the proximal end of the guide wire, and the catheter is advanced over and along the guide wire through the vascular system until the distal end of the catheter is located at the remote site. Once the distal end of the catheter is located at the remote site, the guide wire is normally withdrawn through the lumen of the catheter.

To access a remote site in the digestive system, in some cases it is possible to locate the catheter at the remote site without the need for a guide wire to guide the catheter to the remote site. However, in many cases in the digestive system, particularly in the more remote locations, for example, in the intestine, or at locations where the remote site is diseased, or where the catheter must pass through a diseased site in order to gain access to the remote site, it is not possible to guide a catheter to a remote site without the assistance of a guide wire. In many cases, particularly, in the case of a balloon catheter where a number of lumens extending axially through the catheter are required to communicate with an inflatable element, such as a balloon on the distal end of the catheter, the transverse cross-section of the catheter may be such that there is insufficient room for a further lumen to accommodate a guide wire. For example, in the case of a balloon catheter of the type used for measuring the volume or the transverse cross-section of a lumen, a vessel or a sphincter at the remote location, at least two discrete and mutually sealed lumens are required to communicate with the inflatable element. One lumen is required to accommodate wires to axially spaced apart measuring electrodes on a portion of the catheter located within the inflatable element, and a second lumen is required to accommodate an inflating medium to the inflatable element for inflating thereof. In many cases additional discrete and mutually sealed lumens are required, for example, one lumen may be required to inflate the inflatable element with an inflating medium, while another may be required to accommodate the inflating medium during deflating of the inflatable element. In many such cases, with such a number of lumens, all of which require to be sealed there may be insufficient room within the cross-section of the catheter for a further lumen to accommodate a guide wire. Additionally, by virtue of the fact that in such cases all the lumens must be mutually sealed from each other, such lumens are unavailable to accommodate a guide wire. There is therefore a need for a catheter which addresses this problem.

There is also a need for a method for monitoring the transverse cross-sectional area of a stoma in a hollow vessel, for example, a stomach, as the stoma is being formed. Obesity is a serious problem nowadays amongst adults, adolescents, and indeed children. There are many ways of treating an obese subject in order to reduce weight. One such treatment is dieting. However, dieting in seriously obese subjects, in general, has a poor success rate. In such cases surgical procedures tend to be more appropriate. Such surgical procedures, in general, are carried out on the stomach of a subject in order to reduce the size of the stomach, and thereby to reduce the volume of food consumed by the subject. One such surgical procedure is referred to as bariatric surgery during which a gastric by-pass is formed, whereby a portion of the stomach is by-passed. Another such surgical procedure which is referred to as gastric banding requires the formation of a stoma in the stomach intermediate the lower oesophageal sphincter and the intestine. The stoma forms a pouch between itself and the lower oesophageal sphincter in which food is digested. The remaining part of the stomach between the stoma and the intestine becomes ineffective. Thus, gastric banding reduces the effective digestive volume of the stomach, thereby leading to weight loss.

During the procedure to form the stoma, a gastric band is secured around the stomach where the stoma is to be formed. One such gastric band is sold under the Trade Mark LAP-BAND by Allergen, and another such gastric band is sold under the Trade Mark REALIZE BAND by Johnson and Johnson. Such gastric bands comprise a band which is secured around the stomach with a clip adjacent the location at which the stoma is to be formed. An elongated inflatable cuff extends the length of the band, and is located on the band so that when the band is secured around the stomach, the inflatable cuff is located between the band and the stomach. By inflating the cuff with the band secured around the stomach, the cuff acts on the stomach wall, thereby forcing the stomach wall inwardly to form the stoma. The internal transverse cross-sectional area of the stoma is determined firstly, by the amount by which the band is initially tightened around the stomach, and secondly, by the amount by which the cuff is subsequently inflated. Typically, the cuff is inflated by an incompressible fluid, such as a saline solution, and the greater the volume of saline solution pumped into the cuff, the smaller will be the transverse cross-sectional area of the stoma.

It is desirable that the internal transverse cross-section of the stoma when formed is of diameter, which typically lies in the range 5 mm to 15 mm. However, in general, from subject to subject, there is little relationship between the amount by which the inflatable cuff is inflated and the actual internal transverse cross-sectional area of the stoma. This is due largely to the fact that the wall thickness of the stomach varies from subject to subject, and furthermore, the fact that the volume of tissue located within the gastric band will, in general, also vary from subject to subject. A further variable which prevents a relationship being established between the amount by which the cuff is inflated and the actual internal transverse cross-sectional area of the stoma relates to the angle of placement of the gastric band around the stomach.

Thus, since a surgeon does not have access to the interior of the stomach during forming of the stoma, measuring of the internal transverse cross-sectional area of the stoma during inflating of the cuff of a gastric band cannot be carried out. Accordingly, the formation of a stoma in a stomach of a subject is very much a trial and error exercise. Indeed, in general, a subject is required to attend at consultations with the surgeon on a frequent basis after such a procedure has been carried out in order to monitor the progress of the subject and to adjust the amount by which the cuff of the gastric band is inflated in order to alter the internal transverse cross-sectional area of the stoma. Such adjustment can only be made based on a subjective assessment by the subject or the care giver. By further inflating the cuff of the gastric band, the internal transverse cross-sectional area of the stoma is reduced, and by partly deflating the cuff of the gastric band, the internal transverse cross-sectional area of the stoma is increased.

During the surgical procedure to form the stoma, an inflating port for facilitating inflating of the cuff of the gastric band is located adjacent the wall of the abdomen of the subject in order to facilitate inflating and deflating of the cuff at subsequent consultations with a surgeon. Thus, in the event that the stoma is found to be unsuccessful in adequately reducing the volume of food consumed by a subject, the cuff of the band is further inflated in order to reduce the internal transverse cross-sectional area of the stoma. On the other hand, if the effect of the stoma is such as to dangerously depress the appetite of the subject, and in turn, the volume of food being consumed by the subject, the cuff of the gastric band is partly deflated in order to increase the internal transverse cross-sectional area of the stoma.

The need for a subject to attend at frequent consultations with a surgeon subsequent to the carrying out of a procedure to form a stoma in the stomach of the subject in order to set the stoma at the appropriate internal transverse cross-sectional area is undesirable, and furthermore, places a high cost burden on the public health service. There is therefore a need for a method and an apparatus for monitoring the internal transverse cross-section of a stoma in a stomach of a subject and indeed, in any other hollow vessel during the formation of the stoma.

The present invention is directed towards providing a catheter and a balloon catheter which address the problem of catheters and balloon catheters identified above, and the invention is also directed towards providing a method and apparatus for monitoring the transverse cross-section of a stoma being formed in a lumen or vessel, and there is also a need for a method for forming a stoma in a vessel.

BACKGROUND OF THE INVENTION

According to the invention there is provided a balloon catheter comprising an elongated catheter extending between a proximal end and a distal end, an inflatable element defining a hollow interior region located on the catheter, a first lumen extending along the catheter from the proximal end to the inflatable element communicating with the inflatable element for accommodating an inflating medium to the inflatable element, a pressure sensing element communicating with the hollow interior region of the inflatable element for sensing pressure of an inflating medium in the inflatable element, the pressure sensing element being located in a chamber formed in a protective housing located adjacent the inflatable element, the protective housing having a communicating opening communicating the pressure sensing element with the hollow interior region of the inflatable element.

In one embodiment of the invention the protective housing comprises a non-deformable housing.

Preferably, the protective housing is located within the catheter. Advantageously, the protective housing is located within a cavity formed in the catheter, the chamber of the protective housing communicating with the cavity through the communicating opening. Preferably, the cavity in the catheter communicates with the hollow interior region of the inflatable element. Ideally, the cavity, within which the protective housing is located, is located in the catheter within the inflatable element.

In one embodiment of the invention the catheter extends through the inflatable element, and the inflatable element defines with the catheter the hollow interior region as an annular hollow interior region.

In another embodiment of the invention the protective housing comprises an elongated tubular housing. Preferably, the tubular housing terminates in one end in the communicating opening for communicating with the hollow interior region of the inflatable element. Advantageously, the protective housing is of circular transverse cross-section.

In one embodiment of the invention a tubular port extends from the protective housing.

In another embodiment of the invention the tubular port forms the communicating opening.

Preferably, the tubular port extends from the protective housing at an end opposite to the end which terminates in the communicating opening.

Advantageously, the tubular port is adapted for accommodating at least one electrically conductive wire to the pressure sensing element. Preferably, the at least one electrically conductive wire is secured to the protective housing. Advantageously, the at least one electrically conductive wire is secured to the protective housing by an adhesive. Ideally, the at least one electrically conductive wire is secured to the protective housing in the chamber.

In one embodiment of the invention the at least one electrically conductive wire is secured to the protective housing in the tubular port. Alternatively, the at least one electrically conductive wire extends to the pressure sensing element from the proximal end of the catheter.

In another embodiment of the invention the pressure sensing element is located in the chamber to be free floating therein.

In another embodiment of the invention the pressure sensing element comprises a solid state strain gauge.

In a further embodiment of the invention the inflatable element is located on the catheter adjacent the distal end thereof. Preferably, the first lumen extends through the catheter from the proximal end thereof to the inflatable element.

In one embodiment of the invention a measuring means is provided for determining a transverse cross-sectional dimension of the inflatable element. Preferably, the measuring means is located within the inflatable element for measuring a value of a transverse cross-sectional dimension of the inflatable element.

In one embodiment of the invention the measuring means comprises at least one stimulating electrode located within the inflatable element on one of the catheter and the inflatable element for receiving an electrical stimulating signal, and at least one sensing electrode located within the inflatable element on one of the catheter and the inflatable element axially spaced apart from the stimulating electrode, the at least one sensing electrode being responsive to a stimulating signal applied to the at least one stimulating electrode when the inflatable element is inflated with an electrically conductive medium for producing a response signal indicative of a value of the transverse cross-sectional dimension of the inflatable element adjacent the sensing electrode.

Advantageously, a pair of axially spaced apart stimulating electrodes are provided. Preferably, a plurality of axially spaced apart sensing electrodes are provided between the two stimulating electrodes and axially spaced apart therefrom.

In one embodiment of the invention the axial spacing between at least two of the sensing electrodes is greater than the axial spacing between others of the sensing electrodes to increase the sensitivity with which the value of transverse cross-sectional dimension of the inflatable element is determined.

In another embodiment of the invention the axial spacing between the sensing electrodes is greatest at a location where the transverse cross-section of the inflatable element is adapted to be greatest.

In a further embodiment of the invention the axial spacing between the sensing electrodes is greatest at a location where the transverse cross-sectional area of the inflatable element is greatest when in use.

In a further embodiment of the invention the sensing electrodes between which the axial spacing is greatest are located at a position intermediate the axial opposite ends of the hollow interior region of the inflatable element. Alternatively, the sensing electrodes between which the axial spacing is greatest are located adjacent the axial centre of the hollow interior region of the inflatable element.

In another embodiment of the invention the sensing electrodes between which the axial spacing is greatest are located towards at least one axial end of the hollow interior region of the inflatable element.

In a further embodiment of the invention the sensing electrodes between which the axial spacing is greatest are located towards respective axial opposite ends of the inflatable element.

In a further embodiment of the invention the inflatable element when inflated is adapted to be of stepped transverse cross-section, and the sensing electrodes between which the axial spacing is greatest are located adjacent the portion of the inflatable element adapted to be of greatest transverse cross-section when inflated, and the sensing electrodes between which the axial spacing is least are located adjacent the portion of the inflatable element adapted to be of smallest transverse cross-section when inflated.

In another embodiment of the invention the axial spacing between at least three of the sensing electrodes of greatest axial spacing is substantially similar.

Preferably, the axial spacing between at least five of the sensing electrodes of greatest axial spacing is substantially similar.

Advantageously, the axial spacing between the sensing electrodes progressively decreases from the sensing electrodes of greatest axial spacing therebetween to the sensing electrodes of least axial spacing therebetween.

In one embodiment of the invention the greatest axial spacing between the sensing electrodes lies in the range of 5 mm to 10 mm. Preferably, the minimum axial spacing between the sensing electrodes lies in the range of 2 mm to 5 mm.

Preferably, each stimulating electrode is located on the catheter. Advantageously, each sensing electrode is located on the catheter. Preferably, each stimulating electrode comprises a band electrode extending around the catheter. Advantageously, each sensing electrode comprises a band electrode extending around the catheter. Ideally, each band electrode extends completely around the catheter.

In one embodiment of the invention a communicating means is provided for communicating each stimulating electrode with a signal generator remote from the hollow interior region of the inflatable element, and for communicating each sensing electrode with a signal processing means remote of the hollow interior region of the inflatable element.

Preferably, the communicating means comprises a plurality of mutually insulated electrically conductive wires extending from the respective stimulating and sensing electrodes.

Advantageously, a second lumen is provided extending along the catheter from the proximal end thereof to the electrodes for accommodating the wires from the respective electrodes to the proximal end of the second lumen. Preferably, the second lumen extends through the catheter.

In one embodiment of the invention a portion of the second lumen adjacent the inflatable element forms the cavity within which the protective housing is located. Preferably, the electrically conductive wires extending from the pressure sensing element through the protective housing are accommodated through the second lumen to the proximal end of the catheter.

In another embodiment of the invention a temperature sensing means is provided for monitoring the temperature of the pressure sensing element. Preferably, the temperature sensing means is adapted for monitoring the temperature of the inflating medium for facilitating compensating for temperature variation of the pressure sensing element during reading of signals from the pressure sensing element indicative of the pressure of the inflating medium. Advantageously, the temperature sensing means is adapted for monitoring the temperature of the inflating medium for facilitating compensating for temperature variation of the inflating medium when reading signals from the sensing electrodes indicative of the transverse cross-sectional dimension of the inflatable element adjacent the respective sensing electrodes.

In one embodiment of the invention an isolating means is located in the second lumen intermediate the proximal end thereof and the inflatable element for preventing inflating medium exiting through the proximal end of the second lumen.

In another embodiment of the invention a guide wire accommodating lumen extends internally through the catheter.

In an alternative embodiment of the invention a guide wire engaging means is mounted externally on one of the catheter and the inflatable element for engaging a guide wire for guiding of the balloon catheter along the guide wire to a remote site. Preferably, the guide wire engaging means comprises a guide wire engaging element extending from the one of the catheter and the inflatable element. Advantageously, the guide wire engaging element defines a guide wire accommodating opening for slideably accommodating the guide wire therethrough. Ideally, the guide wire accommodating opening is provided by a guide wire accommodating bore extending through the guide wire engaging element. Preferably, the guide wire accommodating bore is sized to form a sliding fit on the guide wire. Advantageously, the guide wire accommodating bore defines a central axis extending parallel to the catheter.

In one embodiment of the invention the guide wire engaging means is mounted on the catheter and extends transversely thereof. Preferably, the guide wire engaging means is located adjacent the distal end of the catheter.

In another embodiment of the invention a plurality of guide wire engaging means are located axially spaced apart along a portion of the catheter. Preferably, the guide wire engaging means are located axially spaced apart along substantially the length of the catheter.

Advantageously, the guide wire engaging means is releasably mounted on the balloon catheter.

In another embodiment of the invention the guide wire engaging means comprises a lumen extending along a portion of the catheter externally thereof.

In a further embodiment of the invention the guide wire engaging means is mounted on the inflatable element.

In one embodiment of the invention the inflatable element comprises a balloon.

The invention also provides in combination a balloon catheter according to the invention and a guide wire engaged in the guide wire engaging means.

The invention further provides a balloon catheter comprising an elongated catheter extending between a proximal end and a distal end, and an inflatable element defining a hollow interior region located on the catheter, a first communicating means for accommodating an inflating medium to the hollow interior region of the inflatable element, a plurality of axially spaced apart measuring electrodes located within the hollow interior region of the inflatable element on one of the catheter and the inflatable element, at least one of the measuring electrodes being a stimulating electrode for receiving a stimulating signal, and a plurality of the measuring electrodes being sensing electrodes, the sensing electrodes being responsive to a stimulating signal being applied to the at least one stimulating electrode when the inflatable element is inflated with an electrically conductive inflating medium for producing response signals indicative of values of a transverse cross-sectional dimension of the inflatable element adjacent the corresponding sensing electrodes, the axial spacing between at least two of the sensing electrodes being greater than the axial spacing between others of the sensing electrodes to increase the sensitivity with which the value of transverse cross-sectional dimension of the inflatable element is determined.

Preferably, the axial spacing between the sensing electrodes is greatest at a location where the transverse cross-section of the inflatable element is adapted to be greatest.

Advantageously, the axial spacing between the sensing electrodes is greatest at a location where the transverse cross-section of the inflatable element is greatest when in use.

The invention also provides a catheter comprising an externally located guide wire engaging means adapted for engaging a guide wire for guiding of the catheter along the guide wire.

Preferably, the guide wire engaging means is adapted to slideably engage the guide wire. Advantageously, the guide wire engaging means comprises a guide wire engaging element extending from the catheter. Preferably, the guide wire engaging element defines a guide wire accommodating opening for slideably accommodating the guide wire therethrough.

Further the invention provides a device for mounting on a catheter externally of the catheter, the device comprising a guide wire engaging means adapted for engaging a guide wire externally of the catheter for guiding of the catheter along the guide wire.

Preferably, the guide wire engaging means is adapted for slideably engaging the guide wire.

Ideally, the device is adapted for releasably engaging the catheter.

The invention also provides a method for accessing a remote site in a body of a human or animal by a catheter, the method comprising passing a guide wire through a lumen, a vessel or a vascular system in the body to the remote site, providing a catheter with an externally located guide wire engaging means mounted on the catheter, engaging the guide wire engaging means with the guide wire, and urging the catheter with the guide wire engaging means engaged on the guide wire along the guide wire through the lumen, vessel or vascular system in the body to the remote site.

Further the invention provides a method for increasing the sensitivity with which a value of a transverse cross-sectional dimension of an inflatable element of a balloon catheter is determined, wherein the balloon catheter comprises an elongated catheter extending between a proximal end and a distal end, and the inflatable element defining a hollow interior region is located on the catheter, a first communicating means being provided for accommodating an inflating medium to the hollow interior region of the inflatable element, a plurality of axially spaced apart measuring electrodes located within the hollow interior region of the inflatable element on one of the catheter and the inflatable element, at least one of the measuring electrodes being a stimulating electrode for receiving a stimulating signal, and a plurality of the measuring electrodes being sensing electrodes on which respective response signals are produced indicative of the value of a transverse cross-sectional dimension of the inflatable element adjacent the corresponding sensing electrodes in response to a stimulating signal being applied to the at least one stimulating electrode when the inflatable element is inflated with an electrically conductive inflating medium, the method comprising providing at least two of the sensing electrodes adjacent a location at which the transverse cross-section of the inflatable element is to be greatest in use, with an axial spacing therebetween greater than the axial spacing between others of the sensing electrodes to thereby increase the sensitivity with which the value of the transverse cross-sectional dimension of the inflatable element is determined adjacent the at least two of the sensing electrodes of the greatest spacing therebetween.

Additionally, the invention provides a method for increasing the accuracy with which the pressure of inflating medium in an inflatable element mounted on a catheter of a balloon catheter is determined, wherein the catheter comprises an elongated catheter extending between a proximal end and a distal end, the inflatable element defining a hollow interior region is located on the catheter, and a first lumen extending along the catheter from the proximal end to the inflatable element accommodates an inflating medium to the inflatable element, the method comprising locating a pressure sensing element in a chamber formed in a protective housing located adjacent the inflatable element, the protective housing having a communicating opening communicating the pressure sensing element with the hollow interior region of the inflatable element.

The invention further provides a method for forming a stoma of a desired internal transverse cross-section in a hollow vessel, the method comprising providing a balloon catheter comprising an elongated catheter extending between a proximal end and a distal end, an inflatable element defining a hollow interior region located on the catheter, a measuring means for determining a value of a transverse cross-sectional dimension of the inflatable element, the method further comprising locating the inflatable element in the hollow vessel adjacent a location at which the stoma is to be formed, inflating the inflatable element to a degree that the inflatable element bears on the vessel adjacent the location at which the stoma is to be formed, operating the measuring means to determine the value of the transverse cross-sectional dimension of the inflatable element adjacent the location at which the stoma is to be formed, and continuously updating the determined value of the transverse cross-sectional dimension of the inflatable element, placing a band around the exterior of the hollow vessel adjacent the location at which the stoma is to be formed, and one of tightening and loosening the band until the determined value of the transverse cross-sectional dimension of the inflatable element adjacent the stoma corresponds with a desired internal transverse cross-section of the stoma.

In one embodiment of the invention the band is partly tightened to produce the stoma of the appropriate desired internal transverse cross-section prior to inflating of the inflatable element in the vessel.

In another embodiment of the invention the inflatable element is inflated prior to tightening of the band.

In another embodiment of the invention the inflatable element is inflated with a predefined volume of an inflating medium.

In a further embodiment of the invention the inflatable element is inflated to a predefined pressure.

In a still further embodiment of the invention the inflatable element is inflated to the predefined pressure prior to tightening of the band and the band is tightened until the stoma is of a desired internal cross-section corresponding to the predefined pressure to which the inflatable element has been inflated which corresponds to the pressure exerted on the stoma by the inflatable element.

Preferably, the predefined pressure to which the inflatable element is inflated is at least 5 mm of mercury.

Advantageously, the predefined pressure to which the inflatable element is inflated is at least 10 mm of mercury.

Ideally, the predefined pressure to which the inflatable element is inflated is at least 15 mm of mercury.

In another embodiment of the invention the measuring means comprises at least one stimulating electrode located within the inflatable element on one of the catheter and the inflatable element, and at least one sensing electrode located within the inflatable element on one of the catheter and the inflatable element axially spaced apart from the stimulating electrode, the method further comprising inflating the inflatable element with an electrically conductive medium, applying a constant current stimulating signal of known value to the at least one stimulating electrode and reading a response signal from the at least one sensing electrode in response to the stimulating signal and determining the value of the transverse cross-sectional dimension of the inflatable element adjacent the at least one sensing electrode from the read response signal.

Preferably, the stimulating signal is applied to the at least one stimulating electrode continuously while the band is being one of tightened and loosened.

Advantageously, the response signal from the at least one sensing electrode is continuously read from the at least one sensing electrode.

In one embodiment of the invention the stimulating signal is applied to the at least one stimulating electrode and the response signal is continuously read from the at least one sensing electrode simultaneously with inflating of the inflatable element.

Advantageously, the stimulating signal is applied to the at least one stimulating electrode and the response signal is read from the at least one sensing electrode simultaneously with tightening of the band around the hollow vessel to form the stoma.

Preferably, the method is adapted for forming a stoma in a stomach of a human or animal body.

In one embodiment of the invention the band is a gastric band comprising an elongated band securable around the stomach, and an inflating cuff extending along the band. Advantageously, the gastric band is secured around the outside of the stomach at a location adjacent to which the stoma is to be formed by the inflatable cuff. Preferably, the gastric band is secured around the outside of the stomach with the inflatable cuff located between the gastric band and the stomach.

In one embodiment of the invention the inflatable cuff is inflated until the internal transverse cross-section of the stoma is of the desired cross-section.

In another embodiment of the invention the transverse cross-sectional dimension of the inflatable element which is determined is one of the diameter and the area of the transverse cross-section of the inflatable element adjacent the stoma.

Preferably, a human sensory perceptible signal indicative of the value of the transverse cross-sectional dimension of the inflatable element is produced from the determined value of the transverse cross-sectional dimension of the inflatable element. Advantageously, the human sensory perceptible signal indicative of the transverse cross-section of the stoma is displayed on a visual display screen. Preferably, the human sensory perceptible signal indicative of the transverse cross-sectional dimension of the inflatable element is displayed in the form of one of an alpha or numeric display. Advantageously, the human sensory perceptible signal indicative of the transverse cross-sectional dimension of the inflatable element is displayed in the form of a graphical representation of a portion of the inflatable element adjacent the stoma.

In one embodiment of the invention the graphical representation is displayed as a two-dimensional longitudinal cross-sectional elevational view of the stoma. Preferably, the graphical representation is displayed as a two-dimensional longitudinal cross-sectional elevational view of the stoma and an adjacent part of the vessel.

In an alternative embodiment of the invention the graphical representation is displayed as a three-dimensional longitudinal view of the stoma and an adjacent portion of the vessel.

The invention also provides a method for monitoring the internal transverse cross-section of a stoma as the stoma is being formed in a vessel, the method comprising providing a balloon catheter comprising an elongated catheter extending between a proximal end and a distal end, an inflatable element defining a hollow interior region located on the catheter, a measuring means for determining a value of a transverse cross-sectional dimension of the inflatable element, locating the inflatable element in the hollow vessel adjacent a location at which the stoma is to be formed, inflating the inflatable element to a degree that the inflatable element bears on the vessel adjacent the location at which the stoma is to be formed, operating the measuring means to determine the value of the transverse cross-sectional dimension of the inflatable element adjacent the location at which the stoma is to be formed, and continuously updating the value of the transverse cross-sectional dimension of the inflatable element adjacent the location at which the stoma is to be formed.

Preferably, the value of the transverse cross-sectional dimension of the inflatable element is displayed, and the displayed value of the transverse cross-sectional dimension of the inflatable element is continuously updated. Advantageously, the pressure of the inflating medium of the inflatable element is monitored during formation of the stoma.

Preferably, the pressure of the inflating medium in the inflatable element is maintained substantially constant during formation of the stoma.

Ideally, the inflating medium in the inflatable element is maintained constant at a predefined pressure during formation of the stoma.

In another embodiment of the invention the predefined pressure to which the inflatable element is inflated is at least 5 mm of mercury. Advantageously, the predefined pressure to which the inflatable element is inflated is at least 10 mm of mercury. Advantageously, the predefined pressure to which the inflatable element is inflated is at least 15 mm of mercury.

The invention also provides apparatus for monitoring the internal transverse cross-section of a stoma in a hollow vessel as the stoma is being formed, the apparatus comprising an elongated catheter extending between a proximal end and a distal end, an inflatable element located on the catheter, the inflatable element being adapted for locating in the vessel adjacent the location at which the stoma is to be formed, a measuring means for determining a value of a transverse cross-sectional dimension of the inflatable element, so that when the inflatable element is located in the vessel adjacent the location at which the stoma is to be formed with the inflatable element inflated to engage the vessel adjacent the location at which the stoma is to be formed, a value of the transverse cross-sectional dimension corresponding to the internal transverse cross-section of the stoma is determined by the measuring means.

In one embodiment of the invention a means is provided for producing a human sensory perceptible signal indicative of the value of the transverse cross-sectional dimension of the inflatable element adjacent the location of the stoma.

Advantageously, a display means is provided for displaying the human sensory perceptible signal indicative of the value of the transverse cross-sectional dimension of the inflatable element adjacent the stoma.

Advantageously, the display means displays the value of the transverse cross-sectional dimension of the inflatable element adjacent the stoma as one of an alpha or a numeric display.

Preferably, the display means displays the transverse cross-section of the inflatable element adjacent the stoma as a graphical representation thereof.

In one embodiment of the invention the graphical representation of the transverse cross-section of the inflatable element adjacent the stoma is a two-dimensional representation of a longitudinal cross-section of the stoma and an adjacent part of the vessel.

In an alternative embodiment of the invention the graphical representation of the value of the transverse cross-section of the inflatable element adjacent the stoma is a three-dimensional graphical representation of a longitudinal cross-section of the stoma and an adjacent part of the vessel.

In another embodiment of the invention the measuring means comprises at least one stimulating electrode located within the inflatable element on one of the catheter and the inflatable element, and at least one sensing electrode located within the inflatable element on one of the catheter and the inflatable element axially spaced apart from the stimulating electrode so that when the inflatable element is inflated with an electrically conductive medium and a constant current signal is applied to the at least one stimulating electrode, a voltage response signal produced on the at least one sensing electrode is indicative of the value of the transverse cross-sectional dimension of the inflatable element adjacent the at least one sensing electrode.

Advantageously, a pressure sensing element is provided for monitoring the pressure of inflating medium in the inflatable element during formation of the stoma.

The invention also provides apparatus for monitoring the internal transverse cross-section of a stoma in a hollow vessel as the stoma is being formed, the apparatus comprising a balloon catheter, the balloon catheter comprising an elongated catheter extending between a proximal end and a distal end, and an inflatable element located on the catheter, the inflatable element being adapted for locating in the hollow vessel adjacent a location at which the stoma is to be formed, at least one stimulating electrode located within the inflatable element on one of the catheter and the inflatable element, and at least one sensing electrode located within the inflatable element axially spaced apart from the stimulating electrode on one of the catheter and the inflatable element, the apparatus further comprising a first inflating means for inflating the inflatable element with an electrically conductive inflating medium to a degree that the inflatable element bears on the vessel adjacent the location at which the stoma is to be formed, a means for applying a current stimulating signal of known value to the at least one stimulating electrode, a means for reading a response signal from the at least one sensing electrode in response to the stimulating signal applied to the at least one stimulating electrode, a means for computing a value of a transverse cross-sectional dimension of the inflatable element adjacent the location at which the stoma is to be formed from the response signal read from the at least one sensing electrode representative of the internal transverse cross-section of the stoma.

Preferably, a means is provided for producing a human sensory perceptible signal indicative of the current value of one of the diameter and the area of the internal transverse cross-section of the location of the vessel at which the stoma is being formed as the stoma is being formed. Preferably, a display means is provided for displaying the value of the one of the diameter and the area of the internal transverse cross-section of the location of the vessel at which the stoma is being formed as the stoma is being formed in one of alpha and numeric characters. Advantageously, the display means is adapted for displaying a graphical representation of the location of the vessel at which the stoma is being formed as the stoma is being formed.

In one embodiment of the invention the graphical representation is a two-dimensional graphical representation. Alternatively, the graphical representation is a three-dimensional representation.

In one embodiment of the invention the apparatus is adapted for producing an alert signal when the value of the one of the diameter and the area of the internal transverse cross-section of the location of the vessel at which the stoma is being formed as the stoma is being formed is equal to a predefined value.

In one embodiment of the invention the apparatus is adapted for monitoring the internal transverse cross-section of a stoma being formed in a stomach, whereby the stoma is being formed by a gastric band having a band for securing around the stomach at a location where the stoma is to be formed, and a means for tightening the band around the stomach to form the stoma, the apparatus further comprising a means for controlling tightening of the gastric band around the stomach, the means for controlling the tightening of the gastric band around the stomach being responsive to the computing means for controlling the tightening of the gastric band to produce the stoma to be of a desired internal transverse cross-section.

Preferably, the means for controlling the tightening of the gastric band is adapted for controlling the tightening of a gastric band of the type comprising a band for locating around the stomach and an inflatable cuff attached to the band for locating between the band and the stomach at the location at which the stoma is to be formed, and the means for controlling the tightening of the gastric band comprises an inflating control means for controlling inflating of the inflatable cuff of the gastric band.

In one embodiment of the invention a volume monitoring means is provided for monitoring the volume of inflating medium in the inflatable cuff of the gastric band.

In another embodiment of the invention a pressure monitoring means is provided for monitoring the pressure of the inflating medium in the inflatable cuff of the gastric band.

Preferably, a means is provided for determining a relationship between change in the internal transverse cross-section of the stoma and change in the tightness of the gastric band.

In one embodiment of the invention the means for determining the relationship between change in the internal transverse cross-section of the stoma and tightness of the gastric band determines the relationship from computed values of the internal transverse cross-section of the stoma computed by the computing means and corresponding tightness values of the gastric band.

Advantageously, the means for determining the relationship between change in the internal transverse cross-section of the stoma and change in the tightness of the band determines the relationship between change in the internal transverse cross-section of the stoma and inflating of the inflatable cuff.

Preferably, the tightness of the gastric band is determined by one of the volume and the pressure of the inflating medium in the inflatable cuff of the gastric band.

Ideally, the means for determining the relationship between change in the internal transverse cross-section of the stoma and change in the tightness of the gastric band determines the change in the internal transverse cross-section of the stoma for each unit of inflating medium delivered into or out of the inflatable cuff of the gastric band.

In one embodiment of the invention the determined relationship between the change in the internal transverse cross-section of the stoma and the tightness of the gastric band is stored in a storing means. Preferably, the relationship between change in the internal transverse cross-section of the stoma and the tightness of the gastric band is stored in the form of a look-up table. Ideally, the look-up table contains values of the internal transverse cross-sectional area or diameter of the stoma against corresponding values of the volume of inflating medium in the inflatable cuff of the gastric band.

In one embodiment of the invention the apparatus is adapted for controlling inflating and deflating of the inflatable cuff of the gastric band to produce the stoma to be of a desired internal transverse cross-section based on the determined relationship between the change in the internal transverse cross-section of the stoma and the tightness of the gastric band.

The advantages of the balloon catheters according to the invention are many. Firstly, the pressure of the inflating medium within the inflatable element of the balloon catheter can be relatively accurately determined. By locating the pressure sensing element within or adjacent the hollow interior region of the inflatable element, the pressure sensing element monitors the pressure of the inflating medium within the hollow interior region of the inflatable element directly, and thus, the pressure of the inflating medium monitored by the pressure sensing element is substantially the true value of the pressure of the inflating medium in the hollow interior region of the inflatable element. By locating the pressure sensing element in the protective housing, the pressure sensing element is decoupled from substantially all and in most cases all pressures and forces other than the pressure of the inflating medium in the hollow interior region of the inflatable element. For example, the protective housing absorbs any pressures which would result from bending, twisting or otherwise deforming the catheter when the protective housing is mounted in or on the catheter. Similarly, when mounted adjacent the inflatable element, the protective housing absorbs any pressures which may be induced therein by pressure of the inflatable element bearing on the protective housing. Thus, the protective housing protects the pressure sensing element from any extrinsic pressures resulting from bending, twisting or otherwise deforming the catheter, and from any such pressures resulting from the inflatable element bearing on the protective housing. Therefore, the signals produced by the pressure sensing element are solely indicative of the pressure of the inflating medium within the hollow interior region of the inflatable element. By providing the protective housing as a non-deformable housing, the pressure sensing element is completely decoupled from all other pressures and forces other than the pressure of the inflating medium within the hollow interior region of the inflatable element.

Secondly, the balloon catheters and the catheters according to the invention are suitable for guiding along an externally located guide wire to a remote site in the body of a human or animal subject.

Thirdly, the sensitivity with which the values of the transverse cross-sectional area or diameter of a vessel of varying transverse cross-sectional area can be determined is significantly improved.

Using the method and apparatus for monitoring the formation of a stoma allows the stoma to be formed more accurately to a desired internal transverse cross-sectional area or diameter, and the method for forming a stoma according to the invention similarly allows the stoma to be formed more accurately to a desired internal transverse cross-sectional area or diameter.

A further advantage of the invention is provided when the apparatus for monitoring the stoma is adapted for determining a relationship between change in the internal cross-section of the stoma and change in the tightness of a gastric band forming the stoma. By determining the said relationship, inflating and deflating of an inflatable cuff of a gastric band used for forming the stoma can be controlled based on the determined relationship between the change in internal transverse cross-section of the stoma and the tightness of the gastric band in order to produce the stoma to a desired internal transverse cross-section.

By storing the determined relationship between the change in the internal transverse cross-section of the stoma and the tightness of the gastric band, subsequent inflation of the gastric band may be controlled based on the said determined relationship for subsequently adjusting the internal transverse cross-section of the stoma without the need to monitor the internal transverse cross-section of the stoma within the stomach. Storing the said determined relationship between change in the internal cross-section of the stoma and the tightness of the gastric band in the form of a look-up table permits both manual and automatic subsequent adjustment of the internal transverse cross-section of the stoma without the need to monitor the internal transverse cross-section of the stoma within the stomach.

BRIEF DESCRIPTION OF THE DRAWINGS

The invention will be more clearly understood from the following description of some preferred embodiments thereof, which are given by way of example only, with reference to the accompanying drawings, in which:

FIG. 4 is an enlarged plan view of a portion of the balloon catheter of FIG. 2, FIG. 5 is a cross-sectional side elevational view of a detail of the balloon catheter of FIG. 2, FIG. 12 is a perspective view of a balloon catheter according to a further embodiment of the invention, FIG. 13 is a partly cross-sectional plan view of the balloon catheter of FIG. 12, FIG. 14 is a top plan view of the balloon catheter of FIG. 12 in use, FIG. 15 is a side elevational view of a portion of a balloon catheter according to another embodiment of the invention, FIG. 16 is a side elevational view of a portion of a balloon catheter according to another embodiment of the invention, FIG. 17 is a side elevational view of a portion of a balloon catheter according to another embodiment of the invention, FIG. 18 is a side elevational view of a portion of a balloon catheter according to another embodiment of the invention, FIG. 19 is a side elevational view of a portion of a balloon catheter according to another embodiment of the invention, FIG. 20 is a view similar to FIG. 19 of the balloon catheter of FIG. 19 in use.

DETAILED DESCRIPTION OF THE INVENTION

Figure 1:
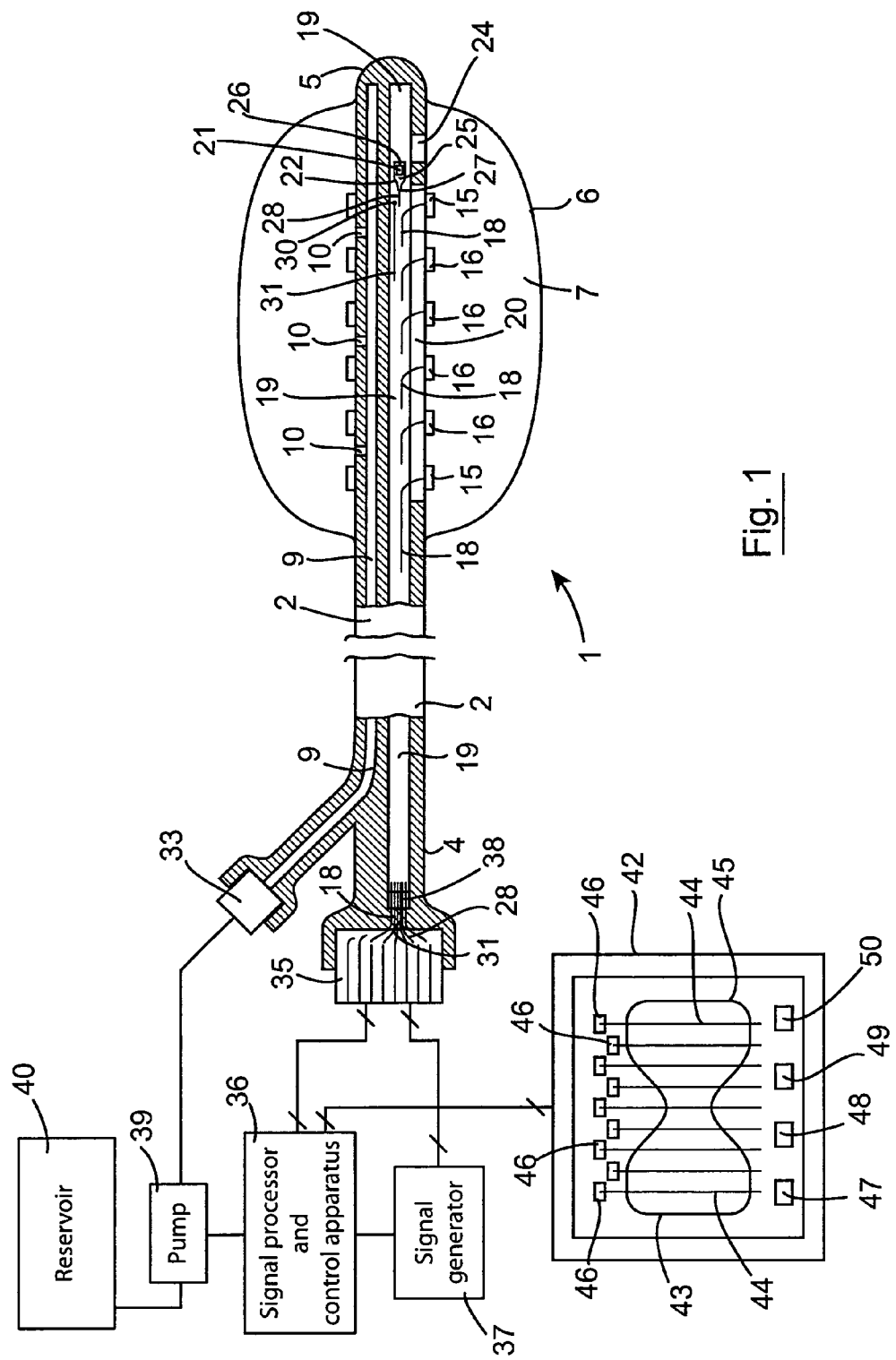
FIG. 1 is a block representation of apparatus according to the invention for determining values of the transverse cross-sectional area of a lumen or vessel and for determining the volume of the lumen or vessel.
Figure 2:
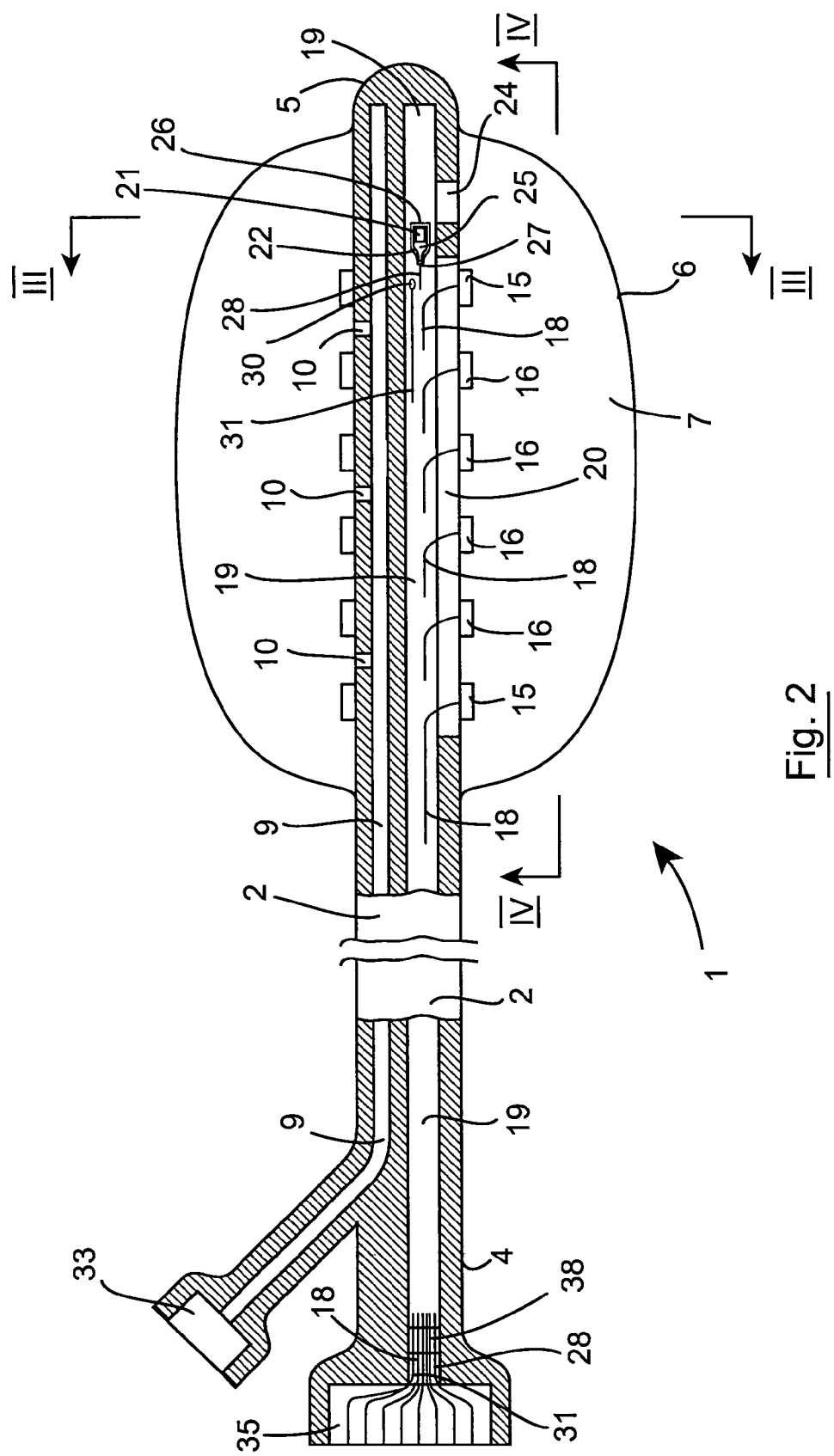
FIG. 2 is a cross-sectional side elevational view of a balloon catheter also according to the invention of the apparatus of FIG. 1.
Figure 7:
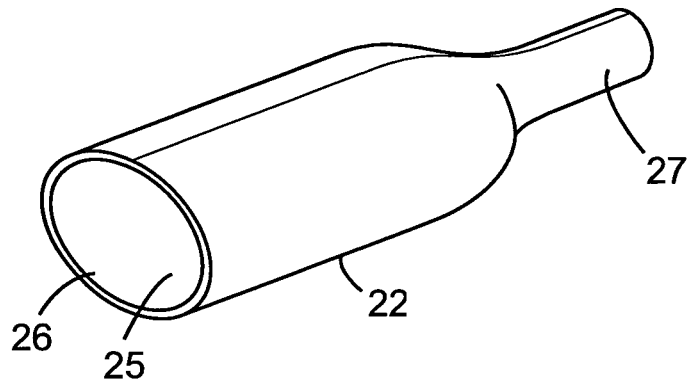
FIG. 7 is a perspective view of a portion of the balloon catheter of FIG. 2.
Figure 3:
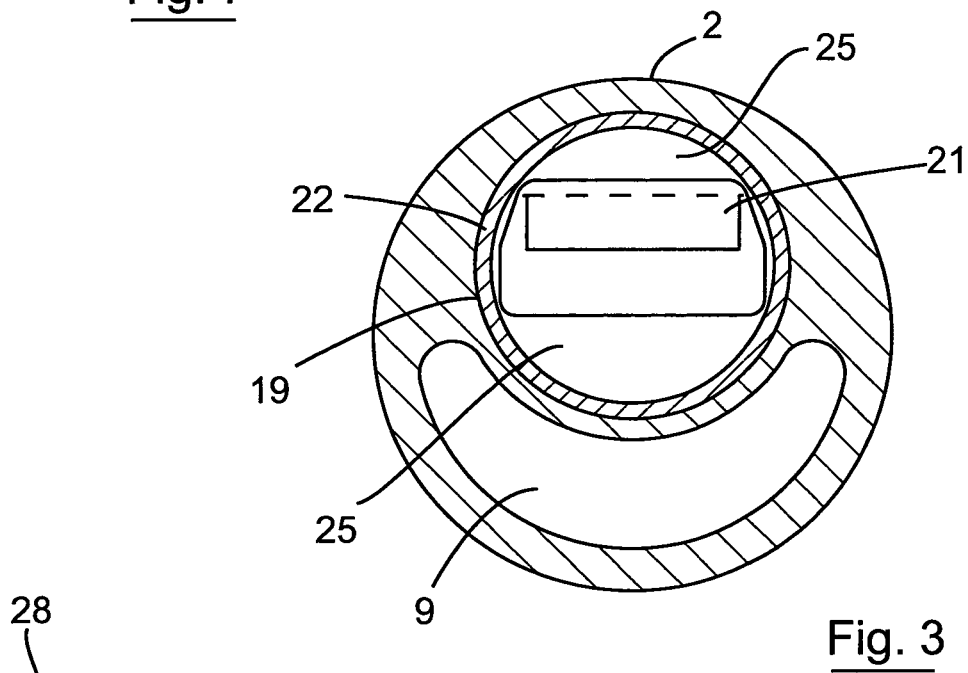
FIG. 3 is a transverse cross-sectional end elevational view of a portion of the balloon catheter of FIG. 2 on the line III-III of FIG. 2.
Figure 6:
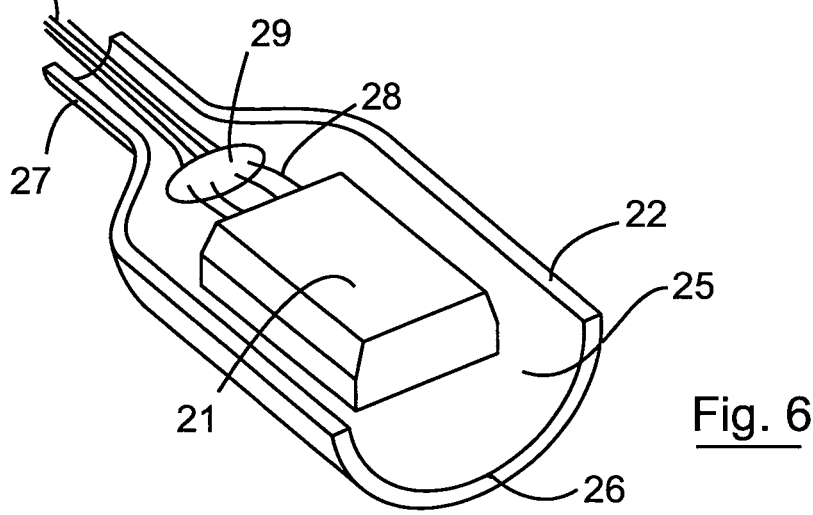
FIG. 6 is a perspective view of a detail of the balloon catheter of FIG. 2.

Referring to the drawings and initially to FIGS. 1 to 7 thereof, there is illustrated apparatus according to the invention comprising a balloon catheter also according to the invention, indicated generally by the reference numeral 1 for accessing a remote site in a body of a human or animal subject. The balloon catheter 1 is particularly suitable for use in a method for forming a stoma in the stomach of a human subject and for monitoring the internal transverse cross-sectional dimension, such as the internal transverse cross-sectional area or diameter of the stoma during formation thereof. The formation of a stoma in the stomach of a human or animal subject will be described in more detail below. However, it will be readily apparent to those skilled in the art that the balloon catheter 1 may be used for many other purposes, where it is desired to determine a value of a transverse cross-sectional dimension such as the diameter and/or the area of a lumen, a vessel, a sphincter or other such hollow organ, for example, in the formation of a gastric sleeve. The balloon catheter 1 is also suitable for determining the volume of a lumen, a vessel or other hollow organ or a part thereof. Before describing the apparatus, the balloon catheter 1 will first be described.

The balloon catheter 1 comprises an elongated catheter 2 extending between a proximal end 4 and a distal end 5. An inflatable element, in this embodiment of the invention a balloon 6 is located on the catheter 2 towards the distal end 5 thereof, and the catheter 2 extends through the balloon 6, so that the balloon 6 defines with the catheter 2 an annular hollow interior region 7 extending around the catheter 2. A first lumen 9 extends through the catheter 2 from the proximal end 4 to the balloon 6, and communicates with the hollow interior region 7 of the balloon 6 through a plurality of radial bores 10 for accommodating an inflating medium to and from the hollow interior region 7 of the balloon 6 for inflating and deflating the balloon 6. The radial bores 10 extend through the catheter 2 from the first lumen 9 to the hollow interior region 7 of the balloon 6. The first lumen 9 is sealed at the distal end 5 of the catheter 2.

A measuring means for determining the diameter, the transverse cross-sectional area and/or the volume of the balloon 6 comprises a plurality of measuring electrodes, namely, a pair of axially spaced apart stimulating electrodes 15 located on the catheter 2 within the hollow interior region 7 of the balloon 6, and a plurality of axially equi-spaced apart sensing electrodes 16 located also on the catheter 2 within the hollow interior region 7 of the balloon 6 and axially spaced apart from and located between the stimulating electrodes 15. A communicating means, namely, a plurality of electrically conductive wires 18 from the stimulating and sensing electrodes 15 and 16 are accommodated through a second lumen 19 to the proximal end 4 of the catheter 2. An elongated longitudinally extending slot 20 is formed in the catheter 2 within the balloon 6, and communicates with the second lumen 19 for accommodating the wires 18 from the stimulating and sensing electrodes 15 and 16 into the second lumen 19. In this embodiment of the invention one wire is provided for each one of the stimulating electrodes 15 for applying a constant current stimulating signal of known current value to the stimulating electrodes 15 and one wire 18 is provided for each of the sensing electrodes 16 so that voltage response signals, which are produced on the sensing electrodes 16 in response to the stimulating signal, and which are indicative of values of the transverse cross-sectional area of the inflatable element 6 adjacent the respective sensing electrodes 16 when the inflatable element 6 is inflated with an electrically conductive medium, may be read from the sensing electrodes 16 in order to determine the values of the transverse cross-sectional area of the inflatable element 6. This aspect of the balloon catheter is described in more detail below. Each stimulating and sensing electrode 15 and 16 is provided by a band electrode of an electrically conductive foil material which extends completely around the catheter 2. The second lumen 19 is sealably closed at its distal end.

A pressure sensing means, namely, a pressure sensing element 21 for monitoring the hydrostatic pressure of inflating medium in the hollow interior region 7 of the balloon 6 is housed in a protective housing 22, which in turn is located in a cavity in the catheter 2 within the balloon 6. In this embodiment of the invention the cavity in which the protective housing 22 is located is provided by the second lumen 19, although the protective housing 22 may be located in a dedicated cavity in the catheter 2 within the balloon 6. The protective housing 22 is located in the second lumen 19 adjacent the distal end 5 of the catheter 2 within the balloon 6. A communicating port 24 extending radially through the catheter 2 from the second lumen 19 communicates the pressure sensing element 21 with the hollow interior region 7 of the balloon 6.

The protective housing 22 is formed of a non-deformable material, which in this embodiment of the invention is of stainless steel material, in order to decouple the pressure sensing element 21 from substantially all extrinsic pressures and forces other than the pressure of the inflating medium in the hollow interior region 7 of the balloon 6. Accordingly, any bending, twisting or any other deforming of the catheter 2 has no effect on the pressure sensing element 21, and signals produced by the pressure sensing element 21 are indicative of the true pressure of the inflating medium in the hollow interior region 7 of the balloon 6. In this embodiment of the invention the pressure sensing element 21 comprises a strain gauge in the form of a solid state device.

The protective housing 22 is of hollow tubular construction of circular transverse cross-section, and defines a chamber 25 also of circular transverse cross-section within which the pressure sensing element 21 is located. The tubular protective housing 22 terminates at one end in a circular communicating opening 26 which communicates the chamber 25 with the second lumen 19, which in turn communicates with the hollow interior region 7 of the balloon 6 through the communicating port 24 in the catheter 2.

A tubular port 27 extending from the protective housing 22 at the opposite end thereof to that of the communicating opening 26 accommodates a plurality of electrically conductive wires 28 from the pressure sensing element 21 into the second lumen 19 in the catheter 2, and in turn to the proximal end 4 of the catheter 2. The wires 28 are secured to the protective housing 22 within the chamber 25 by an adhesive 29 in order to avoid any stresses or strains in the wires 28 being transferred to the pressure sensing element 21. In this embodiment of the invention the pressure sensing element 21 is allowed to float freely in the chamber 25. However, in certain embodiments of the invention it is envisaged that the pressure sensing element 21 may be secured to the protective housing 22 within the chamber 25 by, for example, a suitable adhesive.

Additionally, in this embodiment of the invention a temperature sensing means, namely, a temperature sensor 30 is located in the second lumen 19 adjacent the protective housing 22 for monitoring the temperature of the inflating medium, and in turn the temperature of the pressure sensing element 21 through the inflating medium. Electrically conductive wires 31 from the temperature sensor 30 are accommodated through the second lumen 19 to the proximal end 4 of the catheter 2.

The proximal end 4 of the catheter 2 terminates in a fluid coupling socket 33 into which the first lumen 9 terminates for coupling the first lumen 9 to a source of the inflating medium for inflating and deflating the balloon 6. The proximal end 4 of the catheter 2 also terminates in a pin connector 35 to which the wires 18 from the stimulating and sensing electrodes 15 and 16 are connected. The wires 28 from the pressure sensing element 21 and the wires 31 from the temperature sensor 30 are also connected to the pin connector 35. The pin connector 35 is adapted for coupling of the sensing electrodes 16, the pressure sensing element 21 and the temperature sensor 30 to a signal processing means, namely, a signal processing and control apparatus 36, and for coupling the stimulating electrodes 15 to a signal generating means, namely, a signal generator 37. Both the signal processing and control apparatus 36 and the signal generator 37 are illustrated in block representation only in FIG. 1.

An isolating means, namely, a sealing plug 38 located in the second lumen 19 adjacent the proximal end 4 of the catheter 2 sealably accommodates the wires 18, 28 and 31 therethrough, and sealably closes the second lumen 19 for preventing leaking of the inflating medium from the second lumen 19.

The signal generator 37 is provided for applying the constant current stimulating signal of known value to the stimulating electrodes 15 under the control of the signal processing and control apparatus 36 when the balloon 6 is inflated or being inflated or being deflated with an electrically conductive liquid inflating medium, typically a saline solution. A first inflating medium delivery means comprising a first pump 39 illustrated in block representation in FIG. 1 is operated under the control of the signal processing and control apparatus 36 for inflating and deflating the balloon 6 with the liquid inflating medium from a first reservoir 40 of the electrically conductive liquid inflating medium. However, instead of the first pump 39, the inflating medium delivery means may be provided by a suitable hand operated syringe for manually delivering the liquid inflating medium to and from the balloon 6. The signal processing and control apparatus 36 simultaneously with controlling the signal generator 37 for applying of the constant current stimulating signal to the stimulating electrodes 15 reads the voltage response signals produced on the sensing electrodes 16 when the balloon 6 is inflated with the electrically conductive liquid inflating medium. The signal processing and control apparatus 36 determines the values of the transverse cross-sectional area of the balloon 6 adjacent the respective sensing electrodes 16 from the voltage response signals read from the sensing electrodes 16 as is described in PCT published Patent Application Specification No. WO 2009/001328. Once the values of the transverse cross-sectional area of the balloon 6 adjacent the respective sensing electrodes 16 have been determined, the volume of the balloon 6 is determined by the signal processing and control apparatus 36 from the values of the transverse cross-sectional area of the balloon 6 as is described in PCT Published Application Specification No. WO 2009/001328.

Signals on the wires 28 from the pressure sensing element 21 are read by the signal processing and control apparatus 36 for determining the pressure of the inflating medium in the hollow interior region 7 of the balloon 6.

Signals from the temperature sensor 30 are read by the signal processing and control apparatus 36 for determining the temperature of the inflating medium, and in turn the temperature of the pressure sensing element 21. The signal processing and control apparatus 36 when computing the pressure of the liquid inflating medium from signals read from the pressure sensing element 21 corrects for temperature variations of the pressure sensing element 21. Additionally, when computing the values of the transverse cross-sectional area of the balloon 6 adjacent the sensing electrodes 16 and in turn the volume of the balloon 6, the signal processing and control apparatus 36 corrects for temperature variations in the liquid inflating medium.

A visual display unit 42 comprising a visual display screen 43 is operated under the control of the signal processing and control apparatus 36 for displaying a graphical representation 45 of the inflated balloon 6. In this embodiment of the invention the graphical representation 45 of the inflated balloon 6 is a two-dimensional longitudinal cross-section of the balloon 6. However, the signal processing and control apparatus may be programmed to display a three-dimensional representation of the inflated balloon 6. Line representations 44 of the sensing elements 16 corresponding to their locations relative to the balloon 6 are displayed with the graphical representation 45 of the balloon 6 on the visual display screen 43. The values of the transverse cross-sectional area of the inflated balloon 6 adjacent the respective sensing electrodes 16 are displayed in windows 46 on the visual display screen 43 adjacent the corresponding line representations 44 of the sensing electrodes 15. The total volume of the inflated balloon 6 is displayed in a window 47. The pressure of the inflating medium in the balloon 6 is displayed in a window 49, while the temperature of the inflating medium in the balloon 6 is displayed in a window 50 in the visual display screen 43.

The signal processing and control apparatus 36 is also programmed to compute the partial volume of the balloon 6 between any two selected sensing electrodes 16, and the partial volume is displayed in the window 48. A suitable input means (not shown) is provided for facilitating inputting of selected ones of the sensing electrodes 16 between which the partial volume of the balloon 6 is to be computed. The input means may be provided by a keypad with numbered keys which would correspond to a numbering system of the line representations 44 of the sensing electrodes 16, displayed on the visual display screen 43, or alternatively, the visual display screen 43 could be provided in the form of a touch screen which would facilitate selection of the sensing electrodes 16 by selecting the corresponding line representations 44 of the sensing electrodes 16 by merely touching the appropriate two line representations 44 to be selected.

In use, when it is desired to determine the values of the transverse cross-sectional area and/or the volume of a lumen or a vessel, the balloon catheter 1 is inserted into the lumen or vessel with the balloon 6 located in the lumen or vessel or the part thereof, the values of the transverse cross-sectional area and/or the volume of which are to be determined. The first pump 39 is operated under the control of the signal processing and control apparatus 36 to commence inflating the balloon 6 with the electrically conductive liquid inflating medium. During inflating of the balloon 6, signals from the pressure sensing element 21 are continuously read by the signal processing and control apparatus 36 for monitoring the pressure of the inflating medium in the balloon 6 in order to determine when the balloon 6 has been inflated to a stage where it fills the lumen or vessel without dilating the lumen or vessel, or alternatively is inflated to a target pressure. The value of the pressure of the liquid inflating medium in the balloon 6 is continuously updated in the window 49.

During inflating of the balloon 6 the signal generator 37 is operated to apply the constant current stimulating signal to the stimulating electrodes 15, and the voltage response signals on the sensing electrodes 16 are read by the signal processing and control apparatus 36, which computes the values of the transverse cross-sectional area of the balloon 6 adjacent the sensing electrodes 16. The values of the transverse cross-sectional area of the balloon 6 at locations corresponding to the locations of the sensing electrodes 16 are continuously updated in the corresponding windows 46. The value of the total volume of the balloon 6 is computed by the signal processing and control circuit 36 during inflating of the balloon 6, and the computed value of the total volume of the balloon 6 is continuously updated in the window 47 in the visual display screen 43. The value of the temperature of the liquid inflating medium is also continuously updated in the window 50 during inflating of the balloon 6. The graphical representation of the two-dimensional longitudinal cross-section of the balloon 6 is also continuously updated on the visual display screen 43 during inflating and deflating of the balloon, and/or during variation of the pressure applied externally to the balloon 6 by the vessel or lumen within which the balloon 6 is located for continuously indicating the two-dimensional longitudinal cross-section of the balloon 6.

It has been found that as the balloon 6 is being inflated within a lumen or a vessel, the pressure of the inflating medium in the balloon 6 tends to remain either substantially constant, or increases at a substantially constant rate for each unit volume of the inflating medium delivered into the balloon 6. However, once the balloon 6 fills the cross-section of the lumen or vessel, the pressure of the liquid inflating medium in the balloon 6 begins to either increase, or the rate of increase of the pressure of the liquid inflating medium per unit volume of liquid inflating medium delivered into the balloon 6 commences to increase. Thus, by monitoring the signals from the pressure sensing element 21 during inflating of the balloon 6, the signal processing and control apparatus 36 determines when the balloon 6 has been inflated to just fill the cross-section of the lumen or vessel within which it is located without dilating the lumen or vessel.

Once it has been determined that the balloon 6 fills the cross-section of the lumen or vessel within which it is located, the values of the transverse cross-sectional area of the balloon 6 adjacent the sensing electrodes 16, which correspond to the values of the transverse cross-sectional area of the lumen or vessel adjacent the respective sensing electrodes 16, may be read from the windows 46 in the visual display screen 43. The total volume of the balloon 6, which corresponds to the volume of the lumen or vessel if the balloon 6 fills the lumen or vessel may be read from the window 47 in the visual display screen 43.

In the balloon catheter 1 described with reference to FIGS. 1 to 7, the axial spacing between adjacent ones of the sensing electrodes 16 is similar. Accordingly, the balloon catheter 1 is suitable for determining values of the transverse cross-sectional area of the balloon 6, and in turn a lumen or vessel in which the balloon 6 is located at locations corresponding to the locations of the sensing electrodes 16 where the transverse cross-sectional area of the vessel or lumen does not vary significantly along the longitudinal length thereof. However, in lumens or vessels where the transverse cross-sectional area of the lumen or vessel varies significantly along the longitudinal length of the lumen or vessel, the accuracy with which the values of the transverse cross-sectional area of the lumen or vessel can be determined at locations where the transverse cross-sectional area is relatively large is poor. This is due to the fact that the sensitivity with which the values of the transverse cross-sectional area of the balloon 6 of the balloon catheter 1 can be determined decreases as the transverse cross-sectional area of the balloon increases. This lack of sensitivity results from the fact that the voltage drop in the voltage signals, which are produced on the sensing electrodes 16, between adjacent ones of the sensing electrodes 16 is relatively small at locations where the transverse cross-sectional area of the inflated balloon 6 is relatively large. The small voltage drop in the voltage signals between adjacent ones of sensing electrodes 16 at locations of the balloon where the transverse cross-sectional area thereof is relatively large in turn results from the fact that the electrical impedance provided by the electrically conductive inflating medium between adjacent ones of the sensing electrodes 16 at locations where the transverse cross-sectional area of the inflated balloon is relatively large is relatively small. However, this problem is overcome by a balloon catheter which will now be described with reference to FIGS. 8 to 11.

Figure 8:
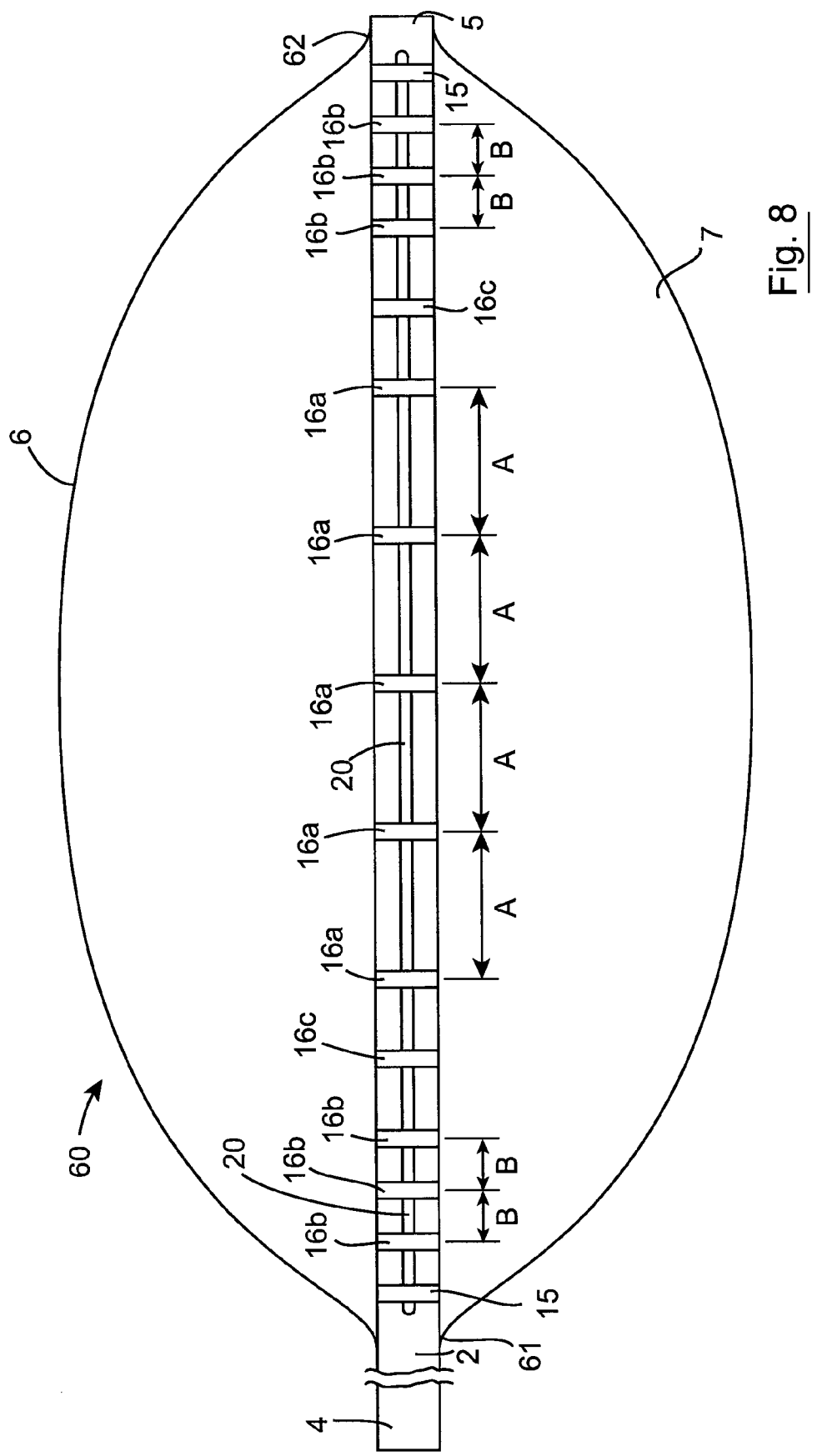
FIG. 8 is a plan view of a portion of a balloon catheter according to another embodiment of the invention.
Figure 9:
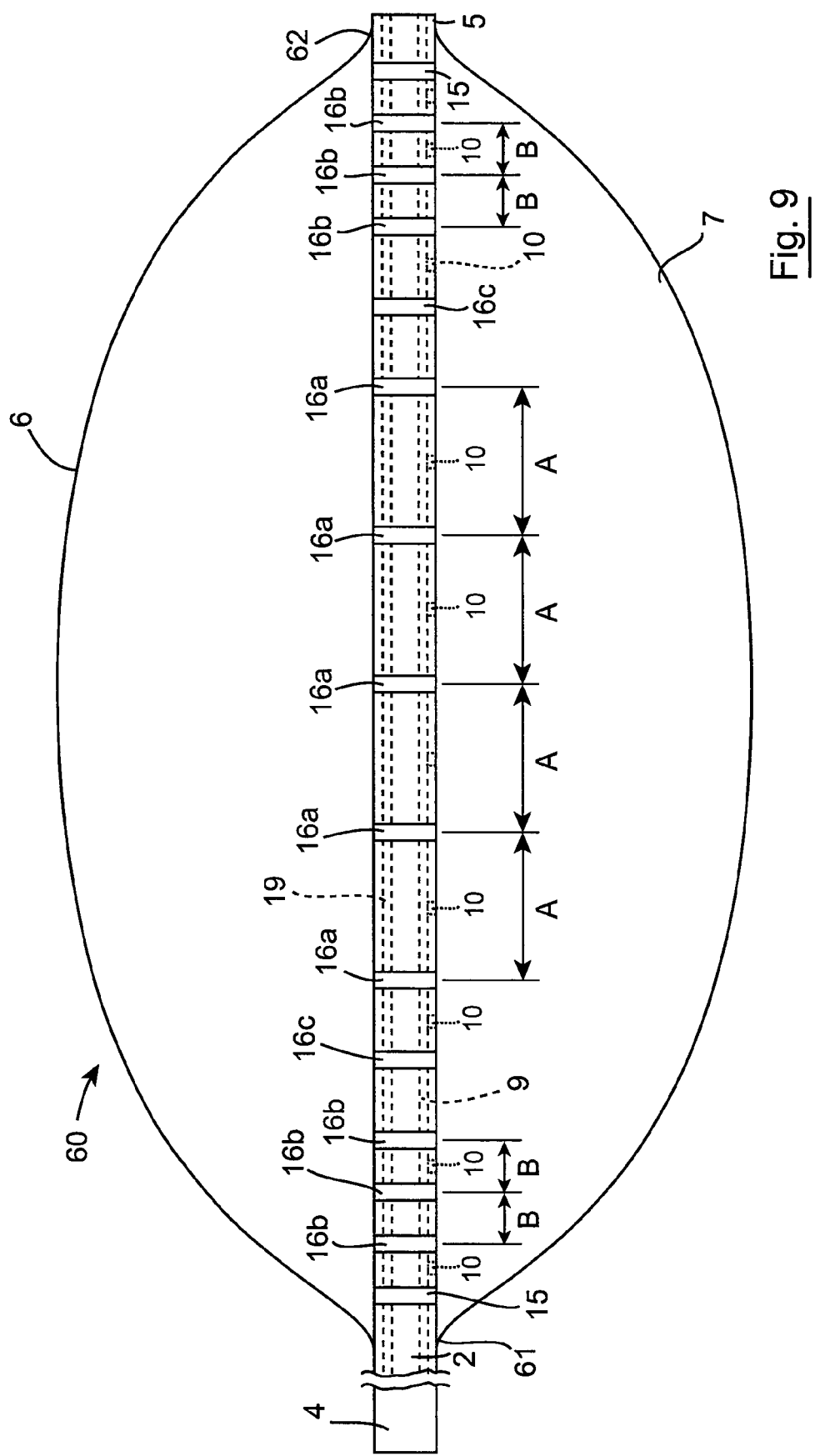
FIG. 9 is a side elevational view of the portion of the balloon catheter of FIG. 8.

Referring initially to FIGS. 8 and 9, there is illustrated a portion of a balloon catheter according to another embodiment of the invention, indicated generally by the reference numeral 60, which is suitable for determining the values of the transverse cross-sectional area and the volume of a lumen or vessel in which the transverse cross-sectional area varies significantly along the axial length of the lumen or vessel.

The balloon catheter 60 is substantially similar to the balloon catheter 1, and similar components are identified by the same reference numerals. In this embodiment of the invention the balloon catheter 60 is suitable for determining the values of the transverse cross-sectional area and the volume of a lumen or vessel in which the axially central portion of the vessel is of transverse cross-sectional area significantly greater than the transverse cross-sectional area of the lumen or vessel towards the axial opposite ends thereof.

The sensing electrodes 16 are located on the catheter 2 with the axial spacing between the sensing electrodes 16 adjacent the axial central portion of the hollow interior region 7 of the balloon 6 being greater than the axial spacing between the sensing electrodes 16 towards respective proximal and distal ends 61 and 62, respectively, of the balloon 6. In this embodiment of the invention the axial spacing A between five of the sensing electrodes 16a in the axial central portion of the hollow interior region 7 of the balloon 6 is greatest. The spacing A between the five sensing electrodes 16a is similar. The axial spacing B between three of the sensing electrodes 16b towards the respective proximal and distal ends 61 and 62 of the balloon 6 is the smallest spacing, and the spacing B between the sensing electrodes 16b is similar. The axial spacing between the sensing electrode 16c and the adjacent one of the sensing electrodes 16a and the adjacent one of the sensing electrodes 16b progressively decreases from the axial spacing A between the sensing electrodes 16a and the axial spacing B between the sensing electrodes 16b. Although in this embodiment of the invention only one sensing electrode 16c is illustrated between the sensing electrodes 16a of greatest axial spacing and the sensing electrodes 16b of smallest axial spacing, in certain cases it is envisaged that more than one sensing electrode will be located between the sensing electrodes 16a and the sensing electrodes 16b, and the axial spacing between the respective sensing electrodes 16c will progressively decrease from the axial spacing A between the sensing electrodes 16a towards the axial spacing B between the sensing electrodes 16b.

It has been found that by providing the sensing electrodes which are located towards the centre of the hollow interior region 7 of the balloon 6 where the transverse cross-sectional area of the balloon 6 is adapted to be greatest, the voltage difference between the voltage response signal produced on the sensing electrodes 16a between adjacent ones of the sensing electrodes 16a is significantly increased over and above that which would be produced if the spacing between the sensing electrodes 16a were similar to the spacing between the sensing electrodes 16b. This spacing arrangement between the sensing electrodes 16 results in the voltage drop between the voltage response signals produced on adjacent ones of the sensing electrodes 16 along the balloon 6 being of substantially similar magnitude. This thus permits the voltage response signals to be amplified to a greater degree to make use of the full range of, for example, an analogue to digital converter in the signal processing and control apparatus, thus improving the sensitivity and accuracy with which the values of the transverse cross-sectional area of the balloon 7 may be computed adjacent the respective sensing electrodes 11.

Although not illustrated in FIGS. 8 and 9, the signal processing and control apparatus of the balloon catheter 60 is similar to the signal processing and control apparatus 36 of the balloon catheter 1 of FIGS. 1 to 7. When determining the transverse cross-sectional area of the balloon 6 from the response signals read from the sensing electrodes 16 and also when determining the volume of the balloon 6, the spacing between the respective sensing electrodes 16 is taken into account by the signal processing and control apparatus 36. In this embodiment of the invention the values of the axial spacings between the respective sensing electrodes 16 are stored in an EPROM located in the pin connector 35 at the proximal end 4 of the catheter 2. The signal processing and control apparatus 36 is programmed to read the values of the axial spacings of the sensing electrodes 16 when the signal processing and control apparatus 36 is connected to the pin connector 35 of the balloon catheter 60.

By increasing the axial spacing between adjacent pairs of the sensing electrodes 16 at axial locations where the transverse cross-sectional area of the balloon 6 is likely to be greatest in use, the electrical impedance of the inflating medium between adjacent ones of the sensing electrodes 16 is increased, thereby the voltage drop between adjacent ones of the sensing electrodes 16 of greatest axial spacing is correspondingly increased. Otherwise, as discussed above, if the axial spacing of the sensing electrodes 16 at locations where the transverse cross-sectional area of the balloon is to be greatest were to be similar to the axial spacing of the sensing electrodes 16 where the transverse cross-sectional area of the inflated balloon 6 is considerably less, the voltage drop between the voltage response signals on adjacent ones of the sensing electrodes 16 at the larger transverse cross-sectional areas of the balloon 6 would be significantly less and almost indiscernible due to the relatively low impedance of the electrically conductive inflating medium between such sensing electrodes.

Although not illustrated, a pressure sensing element similar to the pressure sensing element 21 of the balloon catheter 1 of FIGS. 1 to 7 is located in the second lumen 19 of the balloon catheter 60 within the balloon 6 as described with reference to the balloon catheter 1. A temperature sensor (not shown) which is similar to the temperature sensor 30 of the balloon catheter 1 is also provided in the second lumen 19 of the balloon catheter 60.

In use, the balloon catheter 60 is inserted into the subject and the balloon 6 is located in the vessel or lumen, the volume of which and the values of transverse cross-sectional area of which are to be determined. The balloon 6 is located in the lumen or vessel, so that the portion of the balloon 6 adjacent the sensing electrodes 16a is located in the lumen or vessel at the location thereof of greatest transverse cross-sectional area, and the portions of the balloon 6 adjacent the sensing electrodes 16b are located in the lumen or vessel where the transverse cross-sectional area is relatively small.

Otherwise, the balloon catheter 60 and its use is similar to that of the balloon catheter 1.

Figure 10:
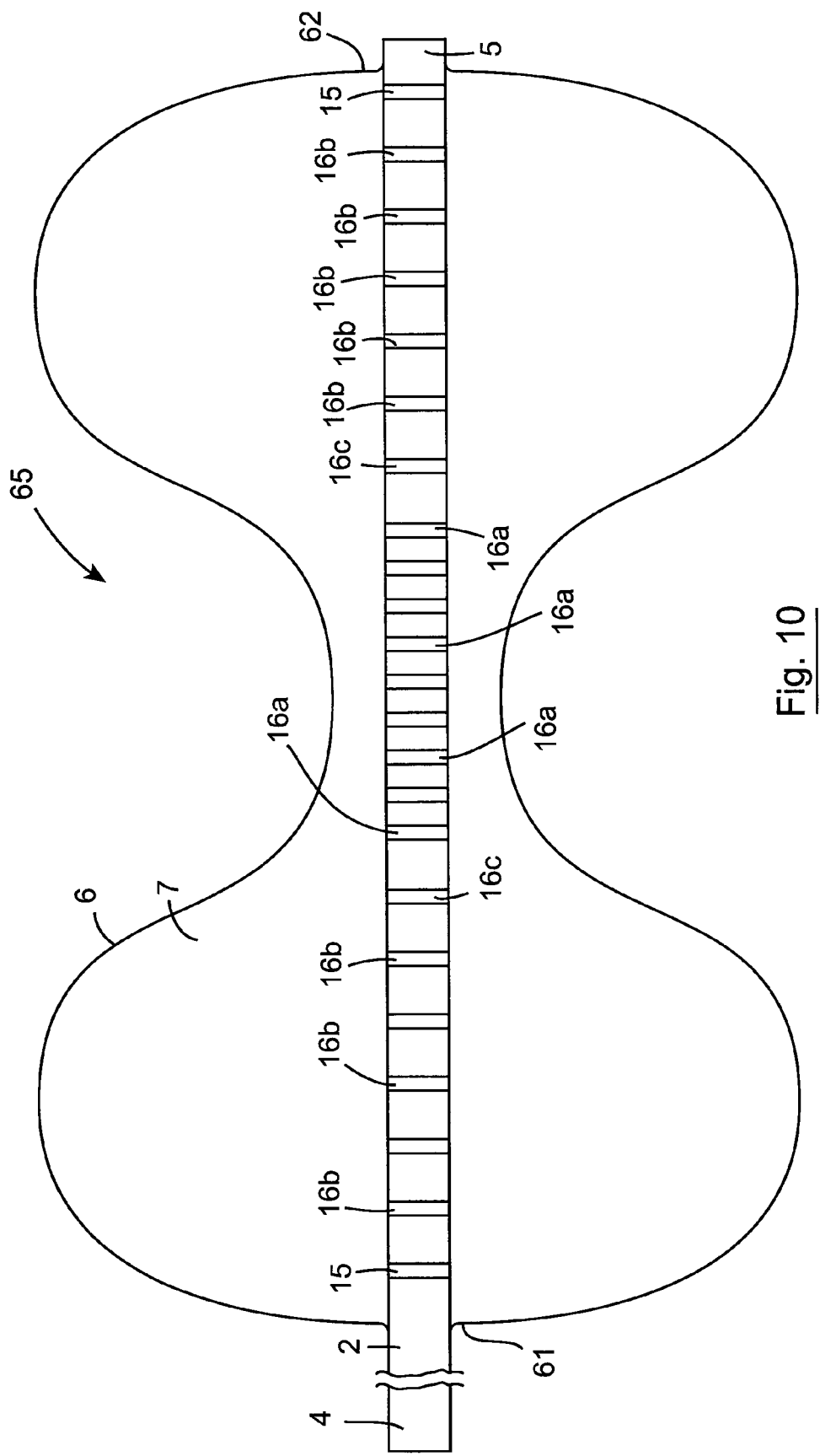
FIG. 10 is a view similar to FIG. 8 of a balloon catheter according to another embodiment of the invention.

Referring now to FIG. 10, there is illustrated a balloon catheter according to another embodiment of the invention, indicated generally by the reference numeral 65, which is suitable for monitoring the internal transverse cross-sectional area of a stoma being formed in a stomach during formation of the stoma, or a sphincter or the like. As mentioned above, the formation of a stoma in the stomach of a human subject will be described in more detail below. The balloon catheter 65 is substantially similar to the balloon catheter 1 and similar components are identified by the same reference numerals. Since the balloon 6 when inserted into the stomach of the human subject will be located such that the stoma will be formed adjacent the axial central portion of the balloon 6, the transverse cross-sectional area of the balloon 6 adjacent the axially central portion thereof during formation of the stoma will be significantly less than the transverse cross-sectional area of the balloon 6 at the respective axial opposite ends thereof. Accordingly, in this embodiment of the invention the axial spacing B between the sensing electrodes 16b towards the respective axial opposite ends of the balloon catheter 6 is greater than the axial spacing A between the sensing electrodes 16a which are located adjacent the axial central portion of the balloon 6. The axial spacing between the sensing electrodes 16c between the adjacent ones of sensing electrodes 16b and the sensing electrodes 16a progressively increases from the sensing electrodes 16a to the sensing electrodes 16b.

Otherwise, the balloon catheter 65 is similar to the balloon catheter 1 and its use is likewise similar.

Figure 11:
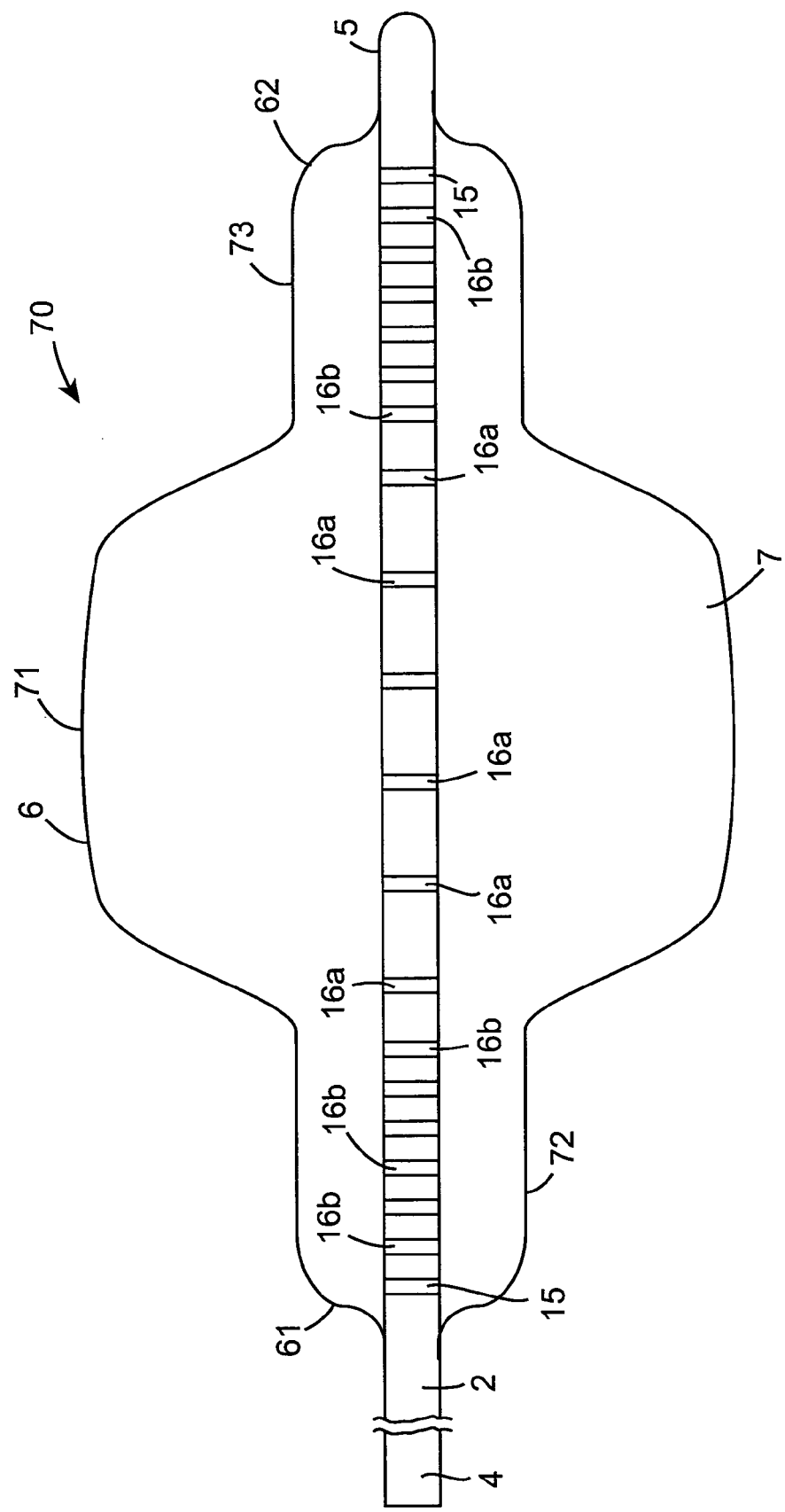
FIG. 11 is a view similar to FIG. 8 of a balloon catheter according to another embodiment of the invention.

Referring now to FIG. 11, there is illustrated a balloon catheter according to another embodiment of the invention which is indicated generally by the reference numeral 70. The balloon catheter 70 is substantially similar to the balloon catheter 1, and similar components are identified by the same reference numerals. The main difference between the balloon catheter 70 and the balloon catheter 1 is that the balloon 6 is shaped so that when inflated the balloon 6 is of stepped transverse cross-sectional area, having a cylindrical axial central portion 71 of relatively large diameter, and cylindrical axial opposite proximal and distal portions 72 and 73, respectively, of significantly smaller diameter to that of the central portion 71 when the balloon 6 is inflated. The balloon catheter 70 is particularly suitable for determining both the volume of a pouch formed in a stomach both during and after bariatric surgery, and also for determining the transverse cross-sectional areas or diameter of the lower oesophageal sphincter and a stoma at the opposite end of the pouch formed during the bariatric surgery. In this case the central portion 71 of the balloon 6 would be located in the stomach at a location where the pouch is to be formed for determining the volume of the pouch. The proximal portion 72 of the balloon 6 would be located in the lower oesophageal sphincter, while the distal portion 73 would be located at the opposite end of the pouch where the stoma is to be formed.

In this embodiment of the invention the sensing electrodes 16b on the catheter 2 adjacent the proximal and distal portions 72 and 73 of the balloon 6 are located relatively close to each other with similar axial spacing between adjacent ones of the sensing electrodes 16b. The sensing electrodes 16a which are located on the catheter 2 adjacent the central portion 71 of the balloon 6 are spaced apart a distance greater than the spacing between the sensing electrodes 16b. In this embodiment of the invention the spacing between adjacent ones of the sensing electrodes 16a is similar and is greater than the spacing between the sensing electrodes 16b. Additionally, in this embodiment of the invention there are no sensing electrodes corresponding to the sensing electrodes 16c of the balloon catheter 60 between the sensing electrodes 16a and 16b whereby the spacing between such electrodes would progressively decrease as in the case of the balloon catheter 60. In the balloon catheter 70 the change in the spacing between adjacent ones of the sensing electrodes 16 is a step change from the sensing electrodes 16a to the sensing electrodes 16b.

In use, to determine the volume of a pouch formed in a stomach during bariatric surgery and to determine the transverse cross-sectional areas or diameters of the lower oesophageal sphincter and a stoma formed at the opposite end of the pouch during the bariatric surgery, the balloon catheter 70 is inserted into the stomach of a subject through the oesophagus with the distal portion 73 of the balloon 6 located adjacent the stoma, the central portion 71 of the balloon 6 located in the pouch and the proximal portion 72 of the balloon 6 located in the lower oesophagus sphincter. The balloon 6 is then inflated with the electrically conductive inflating medium so that the central portion 71 thereof fills the pouch without distending the pouch, and the proximal and distal portion 72 and 73 of the balloon 6 engage the lower oesophagus sphincter and the stoma, respectively without distending either the lower oesophageal sphincter or the stoma. This is achieved by monitoring the pressure of the inflating medium in the balloon 6 as already described with reference to the balloon catheter 1.

The constant current stimulating signal is applied to the stimulating electrodes 15, and voltage response signals which are produced on the sensing electrodes 16 are read by the signal processing and control apparatus, which is similar to the signal processing and control apparatus 36 of the balloon catheter 1. The values of the transverse cross-sectional area or diameter of the balloon 6 adjacent the respective sensing electrodes 16 are computed, and from this the volume of the central portion 71 of the balloon 6, which corresponds to the volume of the pouch is computed. The representation 45 of two-dimensional longitudinal cross-section of the inflated balloon 6 is displayed on the visual display screen 43, and by selecting the sensing electrodes from the line representations 44 of the sensing electrodes 16 which correspond to the proximal and distal ends of the pouch formed in the stomach, the signal processing and control apparatus computes the volume of the balloon 6 between the two selected line representations 44 of the sensing electrodes 16. The volume of the pouch is displayed in the window 48 in the visual display screen 43, while the total volume of the inflated balloon 6 is displayed in the window 47. The values of the transverse cross-sectional area or diameter of the balloon 6 adjacent the corresponding sensing electrodes 16 is displayed in the windows 46. The pressure and temperature of the inflating medium within the balloon 6 is displayed in the windows 49 and 50, respectively.

Otherwise the balloon catheter 70 and its use is similar to the balloon catheter 1.

Referring now to FIGS. 12 to 14 thereof there is illustrated a balloon catheter also according to the invention indicated generally by the reference 75 for accessing a remote site in a body of a human or animal subject. The balloon catheter 75 is substantially similar to the balloon catheter 1 and similar components are identified by the same reference numerals. The main difference between the balloon catheter 75 and the balloon catheter 1 is that it is suitable for engaging an externally located guide wire 76 for facilitating guiding of the balloon catheter 75 to the remote site in the human or animal body through a lumen, vessel or vascular system thereof. In this embodiment of the invention the balloon catheter 75 comprises an end cap 77 which sealably closes the catheter 2 and the first and second lumens 9 and 19 at the distal end 5 of the catheter 2.

A device 78 also according to the invention for engaging the guide wire 76 externally of the balloon catheter 75 comprises a guide wire engaging means provided in the form of a guide wire engaging element 79 located at the distal end 5 of the catheter 2. In this embodiment of the invention the guide wire engaging element 79 extends transversely from the end cap 77 for slideably engaging a guide wire 76 to facilitate guiding the balloon catheter 75 to a remote site along the guide wire 76. The guide wire engaging element 79, in this embodiment of the invention is provided by a guide wire engaging tab 80 of a polymer material which extends radially from the end cap 77. A guide wire accommodating opening, in this embodiment of the invention a guide wire accommodating bore 81 for slideably engaging the guide wire 76 extends through the guide wire engaging tab 80 parallel to the catheter 2. The guide wire accommodating bore 81 is of diameter slightly greater than the diameter of the guide wire 76 to provide an easy sliding fit with the guide wire 76 in the guide wire accommodating bore 81, so that the balloon catheter 75 can be easily slid along the guide wire 76 with the guide wire 76 located in the guide wire accommodating bore 81.

In use, the guide wire 76 is appropriately inserted into an appropriate lumen, vessel, vascular system or the like in the body of a human or animal subject, and is urged through the lumen, vessel or vascular system to the remote site. For example, where the remote site to be accessed is in the digestive system, the guide wire 76 is urged into and through the alimentary tract to the remote site. On the distal end of the guide wire 76 being located at the remote site, the guide wire engaging tab 80 of the balloon catheter 75 is engaged on the guide wire 76 by engaging the proximal end of the guide wire 76 in the guide wire accommodating bore 81 of the guide wire engaging tab 80. The balloon catheter 75 is then urged along the guide wire 76 with the guide wire engaging tab 80 engaged on the guide wire 76 and with the guide wire 76 slideably accommodated in the guide wire accommodating bore 81. The balloon catheter 75 is urged along the guide wire 76 until the balloon 6 of the balloon catheter 75 is located at the remote site adjacent the distal end of the guide wire 76.

Once the balloon 6 of the balloon catheter 75 has been accurately located at the remote site, the guide wire 76, in general, is removed, and the procedure or investigation to be carried out at the remote site is commenced. However, in certain cases, it is envisaged that the guide wire 76 may be left in place during the carrying out of the procedure or investigation, and on completion of the procedure or investigation, the balloon catheter 75 is withdrawn through the alimentary tract along the guide wire 76. However, in general, it is envisaged that the guide wire 76 will be removed prior to carrying out the procedure or investigation, and on completion thereof the balloon catheter 75 is withdrawn through the alimentary tract.

Referring now to FIG. 15, there is illustrated a portion of a balloon catheter according to another embodiment of the invention indicated generally by the reference 85. The balloon catheter 85 is substantially similar to the balloon catheter 1, and similar components are identified by the same reference numerals. The main difference between the balloon catheter 85 and the balloon catheter 1 is that firstly the catheter 2 is provided with a first lumen 9 only which accommodates both the inflating medium for the balloon 6 and the wires (not shown) to the stimulating and sensing electrodes 15 and 16. In this embodiment of the invention the pressure sensing element and the temperature sensor, neither of which are shown, are located in the first lumen 9. Secondly, a device 87 also according to the invention comprising a guide wire engaging means, namely, a guide wire engaging element 88, is provided in the form of a bulbous end cap 89. An elongated catheter engaging bore 90 for sealably engaging the catheter 2 and for sealably closing the first lumen 9 adjacent the distal end 5 of the catheter 2 is sealably engageable on the distal end 5 of the catheter 2. The end cap 89 terminates in a rounded distal leading end 91 for facilitating urging of the balloon catheter 85 through a lumen, vessel or vascular system of the body of a human or animal subject without danger of scratching or injuring the inner surface of the lumen or vessel. An elongated guide wire accommodating bore 92 extends through the end cap 89 for engaging a guide wire, similar to the guide wire 76 of the balloon catheter 75, externally of the balloon catheter 85. The guide wire accommodating bore 92 defines a longitudinally extending axis which extends parallel to the catheter 2, and is of diameter to slideably engage the guide wire.

In use, a guide wire similar to the guide wire 76 is urged through the appropriate lumen, vessel or vascular system of the body of a human or animal subject until the distal end of the guide wire 76 is located at the remote site to be accessed by the balloon catheter 1. The guide wire accommodating bore 92 of the guide wire engaging element 88 is engaged on the proximal end of the guide wire 76, and the balloon catheter 85 is then urged along the guide wire 76 with the guide wire accommodating bore 92 slideably accommodating the guide wire 76 until the balloon 6 of the balloon catheter 85 is located at the remote site. Thereafter the guide wire 76 would typically be removed prior to carrying out the procedure or investigation at the remote site.

Referring now to FIG. 16, there is illustrated a portion of a balloon catheter according to another embodiment of the invention, indicated generally by the reference numeral 95. The balloon catheter 95 is substantially similar to the balloon catheters 1 and 85, and similar components are identified by the same reference numerals as are used with the balloon catheters 1 and 85. The only differences between the balloon catheter 95 and the balloon catheter 85 is that, firstly, in the balloon catheter 95 the guide wire engaging element 88 which is also according to the invention is provided by an end cap 96, which although of different shape to the end cap 89 of the balloon catheter 85 is substantially similar to the end cap 89 of the guide wire engaging element 88 of the balloon catheter 85. Secondly, the catheter 2 of the balloon catheter 95 comprises both first and second lumens 9 and 19, respectively, which are similar to the first and second lumens 9 and 19 of the balloon catheter 1.

Otherwise, the balloon catheter 95 and its use is similar to that of the balloon catheters 1 and 85.

Referring now to FIG. 17, there is illustrated a portion of a balloon catheter according to another embodiment of the invention, indicated generally by the reference numeral 100. The balloon catheter 100 is substantially similar to the balloon catheters 1 and 85, and similar components are identified by the same reference numerals as are used with the balloon catheters 1 and 85. The only difference between the balloon catheter 100 and the balloon catheter 85 is in the shape of the end cap 101 of the guide wire engaging element 88, which is also according to the invention. Otherwise, the balloon catheter 100 and its use is similar to that of the balloon catheter 85.

Referring now to FIG. 18, there is illustrated a portion of a balloon catheter according to a further embodiment of the invention, indicated generally by the reference numeral 105. The balloon catheter 105 is substantially similar to the balloon catheters 1 and 85, and similar components are identified by the same reference numerals as are used with the balloon catheters 1 and 85. The main differences between the balloon catheter 105 and the balloon catheter 85 is firstly in the shape of the end cap 106 of the guide wire engaging element 88, which is also according to the invention, and secondly, the catheter 2 of the balloon catheter 105 is provided with both first and second lumens 9 and 19, respectively.

Referring now to FIGS. 19 and 20, there is illustrated a portion of a balloon catheter according to a still further embodiment of the invention, indicated generally by the reference numeral 110. The balloon catheter 110 is substantially similar to the balloon catheters 1 and 85, and similar components are identified by the same reference numerals as are used with the balloon catheters 1 and 85. The main difference between the balloon catheter 110 and the balloon catheter 85 is in the guide wire engaging element 88 which is also according to the invention. In this case the guide wire engaging element 88 comprises an end cap 111, which in this embodiment of the invention terminates in an elongated distal leading portion 112 which tapers towards a distal leading end 113 which is rounded. A recess 114 extending transversely across the end cap 111 adjacent the leading portion 112 accommodates bending and flexing of the leading portion 112 to facilitate urging the distal end 5 of the balloon catheter 110 around a curved lumen or vessel, and from one lumen or vessel into a branched lumen or vessel.

Otherwise, the balloon catheter 110 and its use is similar to that of the balloon catheter 85.

In the embodiments of the invention described with reference to FIGS. 12 to 20, the guide wire engaging elements 88 of the balloon catheters 75, 85, 95, 100, 105 and 110 are provided as a separate element which can be releasably secured to the distal end 5 of the catheters 2. The guide wire engaging elements 88 are adapted to sealably engage the catheters 2 adjacent the distal ends 5 thereof in order to seal the lumen or lumens extending through the catheters at the distal ends 5 of the catheters 2. By virtue of the fact that the guide wire engaging elements 88 sealably closes the lumens of the catheters 2 at the distal ends 5 thereof, a sealing cap which would otherwise be required at the distal ends 5 of the catheters 2 may be omitted. However, in certain cases, it is envisaged that a separate closure cap or plug may also be provided to sealably close the lumens of the catheters at the distal ends thereof, and the guide wire engaging element would releasably engage the catheter or the closure cap or the plug if appropriate, and in certain cases, the guide wire engaging elements may be adapted to releasably engage only the closure cap.

The advantage of providing the guide wire engaging element as a separate element to the catheter which is releasably engageable with the catheter is that the catheter may be used either with or without the guide wire engaging element. For example, where it is feasible to use an internal lumen of the balloon catheter to engage a guide wire for guiding the balloon catheter over and along the guide wire, the guide wire engaging element may be omitted, while in cases where it is not feasible to use an internal lumen of the balloon catheter to engage a guide wire to guide the catheter over and along the guide wire, the guide wire engaging element may be secured to the distal end of the balloon catheter so that the balloon catheter may be guided along a guide wire externally of the balloon catheter.

Figure 23:
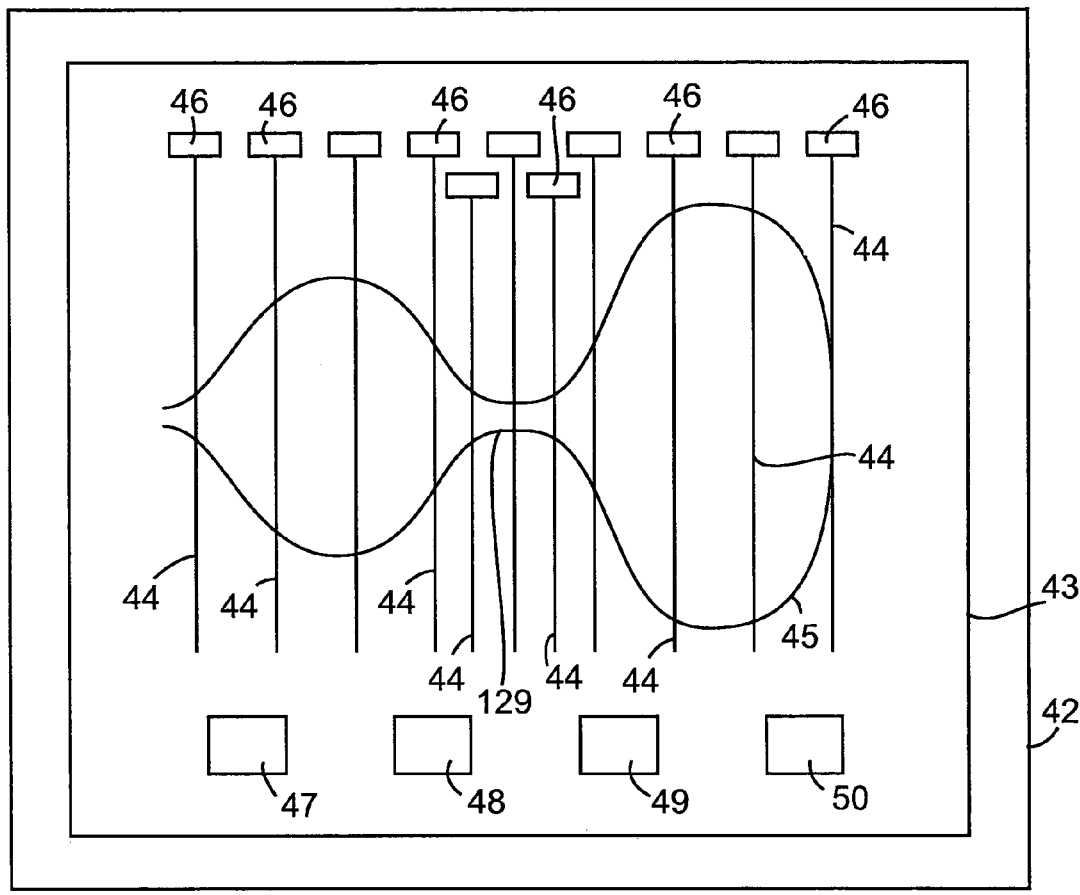
FIG. 23 illustrates a representation of the stoma and a pouch formed in the stomach by the stoma of FIG. 21 illustrated on a visual display screen of the apparatus of FIG. 1.
Figure 21:
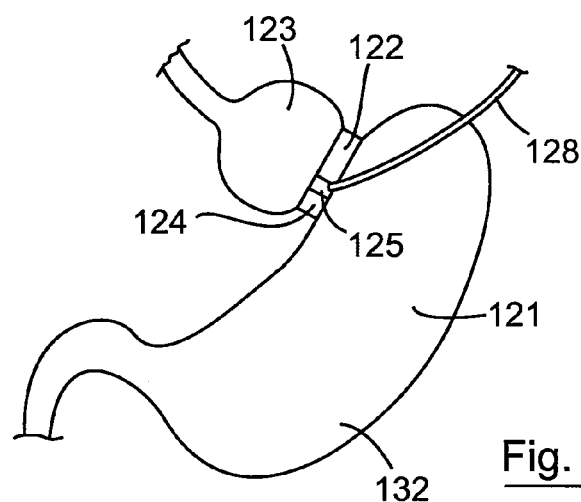
FIG. 21 is a side elevational view of a stoma being formed in a stomach of a human subject.
Figure 22:
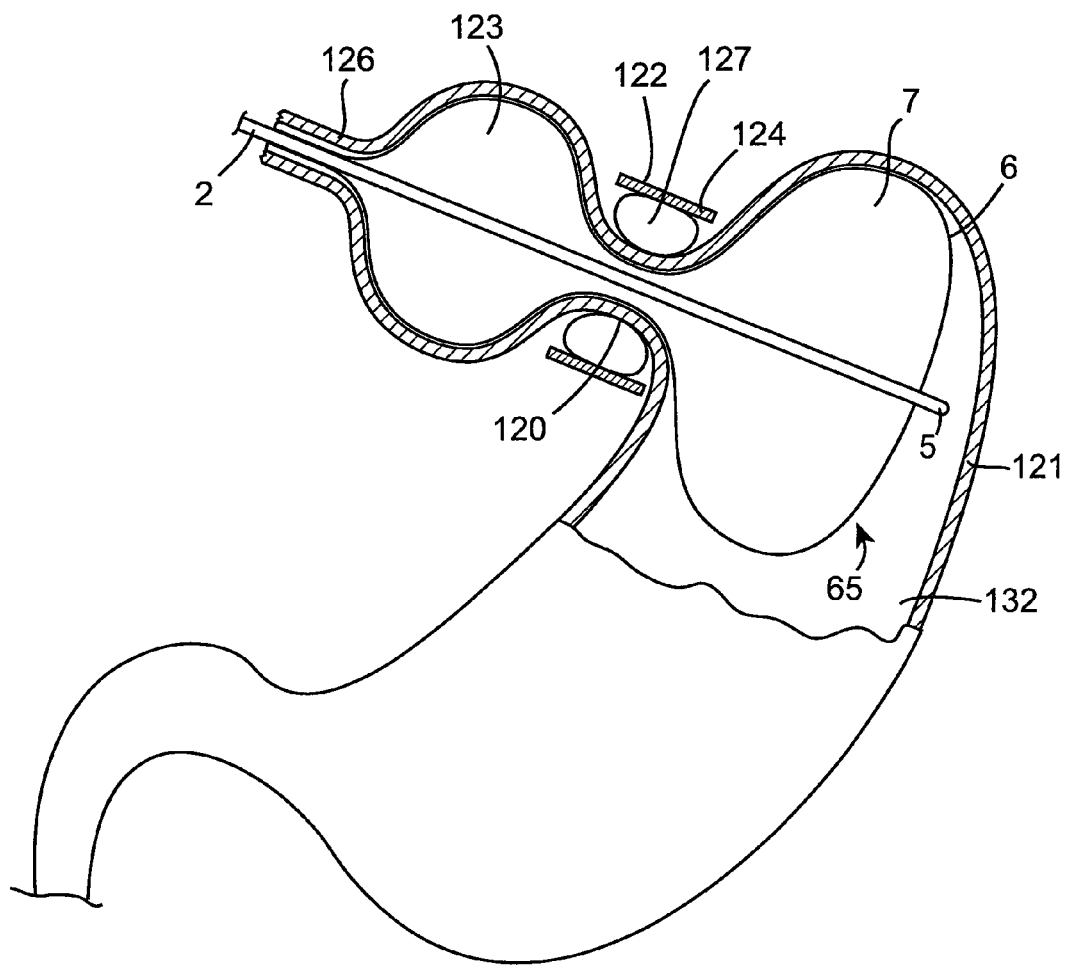
FIG. 22 is a cross-sectional side elevational view of a portion of the stomach of FIG. 21.

Referring now to FIGS. 21 to 23, a method for forming and for monitoring the formation of a stoma 120 in a stomach 121 of a subject using the apparatus described with reference to FIGS. 1 to 7 with the balloon catheter 1 replaced by the balloon catheter 65 will now be described. In the method according to this embodiment of the invention the volume of a pouch 123 formed in the stomach by the stoma 120 between the stoma 120 and the lower oesophageal sphincter 126 is also monitored. In this embodiment of the invention the stoma 120 is formed by a gastric band 122, for example, a gastric band of the type sold under the Trade Mark LAP-BAND by Allergen. The gastric band 122 comprises a band 124 having a clasp 125 for securing the gastric band 122 around the outer surface of the stomach 121 adjacent the location at which the stoma 120 is to be formed. An inflatable cuff 127 extends along the band 124, so that when the gastric band 122 is secured around the stomach 121 by the clasp 125 the inflatable cuff 127 is located between the band 124 and the stomach 121. An inflating tube 128 extending from the inflatable cuff 127 accommodates an inflating medium to the inflatable cuff 127 for inflating thereof. The stoma 120 is initially formed by tightening the band 124 around the stomach 121 to draw in the stomach 121 adjacent the location at which the stoma 120 is to be formed, in order to initially form the stoma 120 to a relatively large diameter, and the band 124 is secured around the stomach 121 by the clasp 125. Thereafter the diameter of the stoma 120 is reduced to the desired diameter by inflating the cuff 127. Inflating of the cuff 127 continues until the internal transverse cross-sectional diameter of the stoma 120 has been reduced to the desired transverse cross-sectional diameter, which typically is in the order of 7 mm. In prior art methods known heretofore, inflating of the inflatable cuff 127 to reduce the internal transverse cross-sectional area of the stoma has been carried out by trial and error methods only. The use of such a gastric band as gastric band 122 will be well known to those skilled in the art.

In this embodiment of the invention prior to attaching the gastric band 122 around the stomach 121, the balloon catheter 65 is inserted either orally or nasally through the oesophagus until the balloon 6 located in the stomach 121 adjacent the location at which the stoma 120 is to be formed. In the balloon catheter 65 as discussed above the axial spacing between the sensing electrodes 16*b* at the axial opposite ends of the balloon 6 is greater than the axial spacing between the sensing electrodes 16*a* adjacent the central portion of the balloon 65. By virtue of the fact that the spacing of the sensing electrodes 16*b* of the balloon catheter 65 towards the proximal end of the balloon 6 are axially spaced apart a distance greater than the axial spacing of the sensing electrodes 16 adjacent the central portion of the balloon 6, the values of the transverse cross-sectional area of the proximal portion of the balloon which corresponds with the pouch 126 can be more accurately determined, and thus the volume of the pouch 126 can similarly be more accurately determined.

When the gastric band 122 has been secured around the stomach 121 by the clasp 125, the cuff 127 is inflated to form the stoma 120 to an internal transverse cross-sectional area which is greater than the desired internal transverse cross-sectional area but is approaching the desired value thereof.

The balloon 6 is then inflated with the electrically conductive liquid inflating medium to fill the transverse cross-section of the stoma 120 and the pouch 123 formed between the stoma 120 and the lower oesophageal sphincter 126, without dilating the stoma 120 or the pouch 123. The constant current stimulating signal is applied to the stimulating electrodes 15. Voltage response signals produced on the sensing electrodes 16 in response to the constant current signal are read by the signal processing and control apparatus 36 which computes the values of the transverse cross-sectional area of the balloon 6 adjacent the respective sensing electrodes 16. The two-dimensional graphical representation 45 of a longitudinal cross-section of the balloon 6 is displayed on a visual display screen 43 of the visual display unit 42, along with the line representations 44 of the sensing electrodes 16, see FIG. 23. The computed values of the transverse cross-sectional area of the balloon 6 adjacent the corresponding sensing electrodes 16, which are similar to the values of the internal transverse cross-sectional area of the stoma 120 and the pouch 123 at locations corresponding to the respective sensing electrodes 16, are displayed in the windows 46 in the visual display screen 43 corresponding to the line representation 44 of the corresponding sensing electrodes 16. In this embodiment of the invention the internal transverse cross-sectional area of the stoma 120 is assumed to be circular, and the values displayed in the windows 46 may be diameter values or area values of the transverse cross-section of the balloon 6.

The sensing electrodes 16 of the balloon catheter 1 which are adjacent the stoma 120 are readily identifiable from the line representations 44 of the sensing electrodes 16 displayed on the visual display screen 43, at the locations 129 of the graphical representation 45 of the balloon 6, where the graphical representation 45 of the balloon 6 necks. Therefore, once the balloon 6 is inflated to fill the transverse cross-section of the stoma 120 and the pouch 123, the values of the transverse cross-sectional area of the stoma 120 may be read from the windows 46 in the display screen 43 corresponding to the line representations 44 of the sensing electrodes 16 adjacent the necked portion 129 of the graphical representation 45 of the balloon 6. Once the balloon 6 engages the stoma 120 the inflatable cuff 127 of the gastric band 122 is then further inflated in order to reduce the internal transverse cross-sectional area of the stoma 120 to the desired internal transverse cross-sectional area, which as discussed above, typically corresponds to 7 mm. On the other hand, if the internal transverse cross-sectional area of the stoma 120 has been over reduced, the inflatable cuff 127 of the gastric band 122 is appropriately deflated to increase the internal transverse cross-sectional area of the stoma 120 to the desired transverse cross-sectional area. During inflating and deflating of the inflatable cuff 127, the graphical representation 45 of the balloon 6 and the values of the transverse cross-sectional area of the balloon 6 in the windows 46 displayed on the visual display screen 43 are continuously updated.

The volume of the pouch 123 is displayed in the window 48 on the display screen 43, by selecting the line representations 44 on the graphical representation 45 of the balloon 6 which define the longitudinal extremities of the pouch 123, and inputting the identities of the two line representations 44 into the signal processing and control apparatus 36.

Alternatively, the balloon 6 may be inflated with the electrically conductive liquid inflating medium once the gastric band 122 has been secured around the stomach 121, and simultaneously with inflating the cuff 127, the constant current stimulating signal would be continuously applied to the simulating electrodes 15 and the resulting voltage response signals would be read from the sensing electrodes 16. The transverse cross-sectional area of the balloon 6 at the sensing electrodes 16 would be computed and continuously updated in the windows 46, and the graphical representation 45 of the balloon 6 would be continuously updated on the visual display screen 43. The surgeon by watching the graphical representation 45 of the stoma 120 and reading the values of the transverse cross-sectional area in the windows 46 would continue inflating the cuff 127 until the value of the internal transverse cross-sectional area of the stoma 120 is of the desired value. In this case, the pressure of the liquid inflating medium in the balloon 6 would be continuously monitored during inflating of the cuff 127 and displayed in the window 49, and any increase in pressure of the liquid inflating medium within the balloon 6 during inflating of the inflatable cuff 127 would be relieved by bleeding liquid inflating medium from the balloon 6. This would avoid any danger of the stoma 120 being formed against a pressure exerted thereon by the balloon 6. The pressure could be automatically monitored by the signal processing and control apparatus 36, which would control operation of the pump 39 for bleeding liquid inflating medium from the balloon 6. Alternatively, the pressure of the liquid inflating medium in the balloon 6 could be observed on the window 49 in the visual display screen 43, and the pump 39 or syringe could be manually controlled.

In a further alternative method for forming the stoma 120, it is envisaged that during inflating of the cuff 127 after the gastric band 122 has been secured around the stomach 121, the liquid inflating medium in the balloon 6 would be maintained at a predefined pressure, which ideally would be of the order of 15 mm of mercury. Inflating of the inflatable cuff 127 would continue until the internal transverse cross-sectional area of the stoma 120 had been reduced to the desired internal transverse cross-sectional area against the pressure of the liquid inflating medium in the balloon 6. This would thus set the maximum diameter to which the stoma 120 would expand in order to accommodate the passage of food therethrough when the food passing through the stoma 120 exerted a pressure on the stoma 120 corresponding to the predefined pressure 15 mm of mercury. It has been demonstrated that a typical intra-bolus pressure, namely, the pressure exerted on a stoma by food passing therethrough would be of the order of 15 mm of mercury. However, this may not always be the case, and may vary from subject to subject, and in which case, the predefined pressure at which the liquid inflating medium would be maintained in the balloon 6 during inflating of the cuff 127 to reduce the diameter of the stoma 120 would vary. The pressure of the liquid inflating medium in the balloon 6 would be maintained during inflating or deflating of the cuff 127 by appropriately bleeding liquid inflating medium from the balloon 6 or pumping liquid inflating medium into the balloon 6, as the case may be, and this could be carried out automatically by the signal processing and control apparatus 36 or manually by observing the pressure of the liquid inflating medium in the window 49 of the visual display screen 43.

On completion of the formation of the stoma 120, the balloon 6 is deflated and the balloon catheter 1 is removed from the subject.

It is envisaged that the signal processing and control apparatus may be programmed to allow the desired value of the internal cross-sectional area or diameter of the stoma, to which the stoma is to be formed, to be entered into the signal processing and control apparatus, so that when the internal cross-section of the stoma is of the desired value, an alert signal would be outputted by the signal processing and control apparatus to indicate to the surgeon that the stoma is of the desired transverse cross-section.

Figure 24:
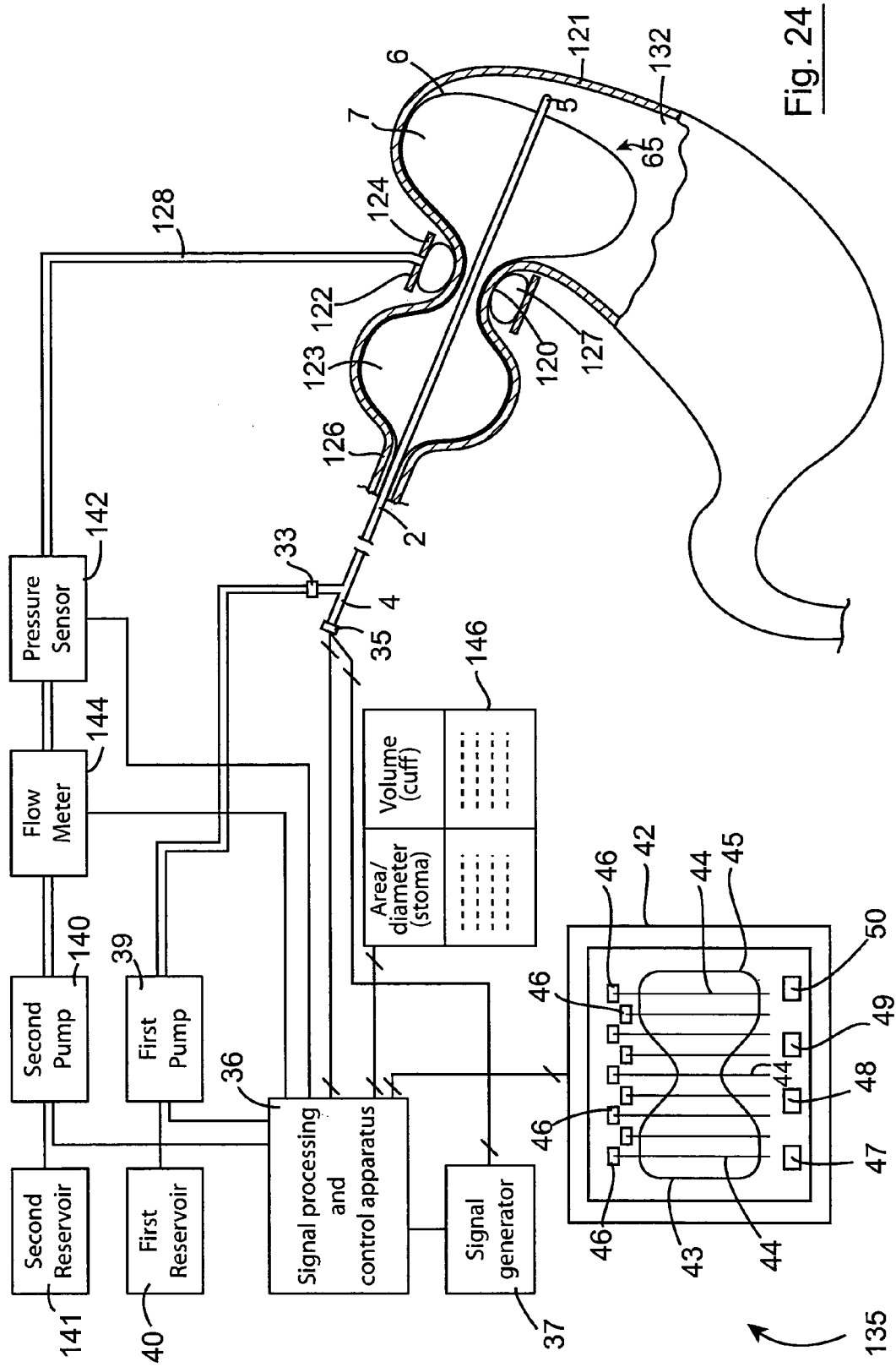
FIG. 24 is a block representation of apparatus according to another embodiment of the invention.

Referring now to FIG. 24, apparatus also according to the invention and indicated generally by the reference numeral 135 is provided for determining values of the transverse cross-sectional area of a lumen or a vessel and for determining the volume of a vessel, which is substantially similar to the apparatus of FIG. 1, and similar components are identified by the same reference numerals. However, in this embodiment of the invention the apparatus is particularly suitable for monitoring the internal transverse cross-section of a stoma being formed in a stomach of a human subject, and also for controlling inflating of an inflatable cuff of a gastric band during formation of the stoma, and controls the inflating of the inflatable cuff in response to the computed internal transverse cross-sectional area or diameter of the stoma which is computed by the signal processing and control apparatus 36. The apparatus 135 will now be described with reference to FIG. 24 and also with reference to FIGS. 21 to 23.

The apparatus 135 comprises an inflating control means comprising a second inflating medium, namely, a second pump 140, which is provided for inflating the inflatable cuff 127 with an inflating medium, for example, a saline solution from a second reservoir 141. The second pump 140 is operated under the control of the process control apparatus 36 for inflating and deflating the inflatable cuff 127 of the gastric band 122.

A pressure sensor 142 is provided for monitoring the pressure of the inflating medium in the inflatable cuff 127, and signals from the pressure sensor 142 are read by the signal processing and control apparatus 36. A flow meter 144 located in the inflating tube 128 between the second pump 140 and the inflatable cuff 127 monitors the flow of inflating medium to and from the inflatable cuff 127, and the signal processing and control apparatus 36 reads signals from the flow meter 144 and is programmed to compute the volume of the inflating medium in the inflatable cuff 127 from the signals read from the flow meter 144.

The signal processing and control apparatus 36 as described with reference to FIGS. 1 to 7 reads the voltage response signals from the sensing electrodes 16 of the balloon catheter 65 and determines values of the transverse cross-sectional area or diameter of the balloon 6 adjacent the respective sensing electrodes 16, which are then displayed on the visual display screen 43 of the visual display unit 42 along with the graphical representation 45 of the balloon 6 and the line representations 44 of the sensing electrodes 16.

The signal processing and control apparatus 36 is also programmed to determine a relationship between change in the internal transverse cross-section of the stoma 120 from signals read from the sensing electrodes 16 adjacent the stoma 120 and the change in tightness of the gastric band 122 resulting from inflating of the inflatable cuff 127. The signal processing and control apparatus 36 determines the relationship by reading values of the sensing electrodes 16 adjacent the stoma 120 and corresponding signals from the flow meter 144 from which the signal processing and control apparatus 36 determines the volume of inflating medium in the inflatable cuff 127 corresponding to the values of the transverse cross-sectional area or diameter of the stoma 120 determined from the signal read from the sensing electrodes 16 adjacent the stoma. The values of the transverse cross-sectional area or diameter of the stoma 120 are stored in a storing means, in this embodiment of the invention a look-up table 146 against corresponding volumes of inflating medium in the inflatable cuff 127. The relationship between the value of the transverse cross-section of the stoma 120 and the tightness of the gastric band 122 is determined from the look-up table 36 by the signal processing and control apparatus 36. By knowing the relationship between the internal transverse cross-section of the stoma and the tightness of the gastric band, subsequent adjustments of the tightness of the gastric band to increase or decrease the internal transverse cross-section of the stoma can be carried out without the need to monitor the internal transverse cross-section of the stoma within the stomach.

The signal processing and control apparatus 36 is also programmed in order to permit inputting of the desired value of the transverse cross-sectional area or diameter of the stoma. Typically, in an adult subject the desired value of the internal transverse cross-sectional diameter of the stoma is in the order of 7 mm. The signal processing and control apparatus 36 is also programmed to determine the location of the stoma by curve fitting or by determining the slope of the graphical representation 45 of the balloon 6.

In this embodiment of the invention prior to attaching the gastric band 122 around the stomach 121, the balloon catheter 65 described with reference to FIG. 10 is inserted either orally or nasally through the oesophagus until the balloon 6 located in the stomach 121 adjacent the location at which the stoma 120 is to be formed. In the balloon catheter 65 as discussed above the axial spacing between the sensing electrodes 16b at the axial opposite ends of the balloon 6 is greater than the axial spacing between the sensing electrodes 16a adjacent the central portion of the balloon 65.

When the desired value of the internal transverse cross-sectional area of the diameter of the stoma has been entered into the signal processing and control apparatus 36, and the gastric band 122 has been secured around the stomach by the clasp 125, the cuff 127 is inflated by the second pump 140 under the control of the signal processing and control apparatus 36 to commence to form the stoma 120.

The balloon 6 is also inflated with the electrically conductive liquid inflating medium under the control of the signal processing and control apparatus 36 to fill the transverse cross-section of the partly formed stoma 120 and the partly formed pouch 123 formed between the stoma 120 and the lower oesophageal sphincter 126 without dilating the partly formed stoma 120 or the partly formed pouch 123.

Voltage response signals produced on the sensing electrodes 16 in response to the constant current signal are read by the signal processing and control apparatus 36 which computes the values of the transverse cross-sectional area or diameter of the balloon 6 adjacent the respective sensing electrodes 16. The two-dimensional graphical representation 45 of a longitudinal cross-section of the balloon 6 is displayed on a visual display screen 43 of the visual display unit 42, along with the line representations 44 of the sensing electrodes 16, see FIG. 23. The computed values of the transverse cross-sectional area of the balloon 6 adjacent the corresponding sensing electrodes 16, which are similar to the values of the internal transverse cross-sectional area of the stoma 120 and the pouch 123 at locations corresponding to the respective sensing electrodes 16, are displayed in the windows 46 in the visual display screen 43 corresponding to the line representation 44 of the corresponding sensing electrodes 16. In this embodiment of the invention the internal transverse cross-sectional area of the stoma 120 is assumed to be circular, and the values displayed in the windows 46 may be diameter values or area values of the transverse cross-section of the balloon 6.

As the inflatable cuff 127 is being inflated, the signal processing and control apparatus 36 determines the location of the stoma and in turn the sensing electrodes 16 adjacent the stoma by determining the slope of the curves of the outline of the graphical representation 45 of the balloon 6. Once the location of the stoma has been determined by the signal processing and control apparatus 26, the signal processing and control apparatus 26 monitors the sensing electrodes 16 which are determined as being adjacent the stoma 120 for in turn determining the internal transverse cross-sectional area or diameter of the stoma 120. The signal processing and control apparatus 36 also determines the location of the lower oesophageal sphincter and the sensing electrode 16 adjacent the lower oesophageal sphincter from the slope of the curves of the outline of the graphical representation of the balloon 6, so that the volume of the pouch 123 can be determined and displayed in the window 48 of the visual display screen 43. The volume of the pouch 123 is similar to the volume of the balloon 6 between the sensing electrodes 16 which are adjacent the stoma 120 and the lower oesophageal sphincter.

As the internal transverse cross-section of the stoma is being reduced, the signal processing and control apparatus 36 prepares the look-up table 36 by storing values of the internal transverse cross-sectional area or diameter of the stoma in the look-up table against the current volume of the inflating medium in the inflatable cuff 127, in order to determine the relationship between the internal transverse cross-section of the stoma and the tightness of the gastric band 124 due to inflating of the inflatable cuff 127. Once an appropriate number of values of the internal transverse cross-sectional area or diameter of the stoma have been stored against the current volume of inflating medium in the inflatable cuff 127, typically, three to five corresponding sets of values, the relationship between the internal transverse cross-sectional area or diameter of the stoma and the tightness of the gastric band 122 can be determined. Thereafter the signal processing and control apparatus 36 operates the second pump 140 to appropriately inflate or deflate the inflatable cuff 127 of the gastric band 122 in response to the computed values of the internal transverse cross-sectional area or diameter of the stoma 120 until the value of the internal transverse cross-sectional area or diameter of the stoma 120 is of the desired value. Thereafter inflating of the inflatable cuff 127 is terminated and the inflating tube 128 is sealed in order to retain the inflatable cuff 127 at the pressure to which it has been inflated. The signal processing and control apparatus 36 may also be programmed to use the relationship determined between the internal transverse cross-section of the stoma and tightness of the gastric band when controlling the second pump 140 to inflate or deflate the inflatable cuff 127 as value of the internal cross-sectional area or diameter of the stoma 120 approaches the desired value.

During formation of the stoma 120 the signal processing and control circuit 36 monitors the pressure of the inflating medium in the balloon 6 by reading signals from the pressure sensing element 21. The first pump 39 is operated under the control of the signal processing and control apparatus 36 for either inflating or deflating the balloon 6 in order to maintain the pressure of the inflating medium in the balloon 6 substantially constant during formation of the stoma 6, and at a pressure which is sufficient to maintain the balloon 6 filling the stoma 120 and the pouch 123 without causing dilation of the stoma or the pouch.

Alternatively, the first pump 39 may be operated during formation of the stoma 120 to maintain the pressure of the inflating medium in the balloon 6 at a predefined pressure, which ideally would be of the order of 15 mm of mercury. In this case inflating of the inflatable cuff 127 by the second pump 140 would continue until the internal transverse cross-sectional area or diameter of the stoma 120 had been reduced to the desired internal transverse cross-sectional area or diameter against the pressure of the inflating medium in the balloon 6. As discussed above, this would thus set the maximum diameter to which the stoma 120 would expand in order to accommodate the passage of food therethrough when the food passing through the stoma 120 exerted a pressure on the stoma 120 corresponding to the predefined pressure 15 mm of mercury, although in some subjects a higher or lower predefined pressure of the inflating medium in the balloon 6 may be desirable, and the signal processing and control apparatus would control the first pump 39 to maintain the pressure of the inflating medium in the balloon 6 at the appropriate predefined pressure.

Once the signal processing and control apparatus 36 has determined the location of the stoma, the signal processing and control apparatus 36 then computes the value of the volume of the balloon between the sensing electrode 16 adjacent the stoma 120 and the sensing electrode adjacent the lower oesophageal sphincter. The volume between these two sensing electrodes is the volume of the pouch, which is displayed on the visual display screen 43 of the visual display unit 42 in the window 48.

On completion of the formation of the stoma 120, the balloon 6 is deflated and the balloon catheter 1 is removed from the subject.

The look-up table 36 and the determined relationship between change in the internal transverse cross-section of the stoma and tightness of the gastric band are stored in the signal processing and control apparatus 36 for that particular subject, and when the subject next presents, for example in one or two weeks' time after the formation of the stoma 120 and the pouch 123, further adjustments of the internal transverse cross-section of the stoma may be made based on the stored relationship between change in the internal transverse cross-section of the stoma and tightness of the gastric band without the need to monitor the internal transverse cross-section of the stoma during adjustment thereof. This, thus, avoids the need to insert a balloon catheter into the stomach during the adjustment. By knowing the change in the internal transverse cross-section of the stoma which results from a unit volume of the inflating means delivered into or delivered out of the inflatable cuff 127, the internal transverse cross-section of the stoma can be readily adjusted to a desired internal transverse cross-sectional area or diameter by delivering an appropriate volume of the inflating medium into or out of the inflatable cuff 127 of the gastric band 122 in order to achieve the desired change in the internal transverse cross-sectional area or diameter of the stoma to in turn produce the stoma of the desired internal transverse cross-sectional area or diameter.

It is envisaged that the signal processing and control apparatus 36 may also be programmed to output an alert signal to indicate to the surgeon that the stoma 120 is of the desired internal transverse cross-sectional area or diameter. This signal could be utilised to cause the value of the internal transverse cross-sectional area of the stoma in the window 46 corresponding to the stoma 120 to flash, thus indicating that the stoma has been formed to the desired internal transverse cross-sectional area or diameter, or the signal may be adapted to produce an audible warning to the surgeon.

While the balloon catheter described for use in the method for forming and monitoring the formation of the stoma has been described as being the balloon catheter 65 according to the invention, any other suitable balloon catheter may be used which included measuring electrodes for facilitating determining of the transverse cross-sectional area of the balloon at axially spaced apart locations.

Indeed, it is envisaged that a balloon catheter could be provided in which the balloon 6 would be of size to fill the entire volume of the stomach, and the spacing of the sensing electrodes 16 would be arranged so that the sensing electrode which would be at a location on the catheter corresponding to the location at which the stoma is to be formed would be spaced apart more closely than the sensing electrodes 16 in the proximal and distal portions of the balloon which would correspond with the pouch 126 to be formed and the remainder of the stomach 132, respectively.

While the method for forming the stoma has been described as forming a stoma in a stomach of a subject, it is envisaged that the method may be used for forming a stoma in the stomach of a human or animal subject. It will also be appreciated that the method according to the invention for forming a stoma may be used for forming a stoma in any hollow vessel, whether it be a biological vessel or otherwise.

While the method for forming the stoma has been described using the balloon catheter 65, any of the other balloon catheters described herein may be used for forming a stoma in a stomach or other vessel or lumen.

While the protective housing for housing the pressure sensing element has been described as being of stainless steel, the protective housing may be of any other suitable metal material, or indeed any other material. For example, it is envisaged that the protective housing may be of a plastics material and may, for example, be formed by injection moulding.

It is also envisaged that the protective housing for housing the pressure element may be located in any suitable location within the balloon or adjacent the balloon, provided of course that the protective housing communicates with the hollow interior region of the balloon. For example, it is envisaged that the protective housing may be mounted externally of the catheter within the balloon, and in which case, it is envisaged that the protective housing would be mounted on the exterior surface of the catheter. The protective housing may also be located in a cavity formed in the catheter which would be specifically formed for the protective housing.

While the protective housing has been described as being of a particular shape and construction, the protective housing may be of any other suitable shape and construction.

While the pressure sensing element has been described as being a solid state strain gauge, any other suitable pressure sensing element or pressure sensing means may be provided. It is envisaged that the pressure sensing element may sense pressure directly or indirectly by directly monitoring pressure or strain as desired.

While the balloon catheters 60 and 70 have been described with five sensing electrodes, namely, the sensing electrodes 16a located in the central portion of the hollow interior region of the balloon which are of greatest axial spacing, many more than five sensing electrodes similar to the sensing electrodes 16a of greatest axial spacing may be provided. The number of sensing electrodes of greatest axial spacing will largely depend on the length of the balloon 6 and maximum diameter to which the balloon 6 is to be inflated. Similarly, while three sensing electrodes, namely, the sensing electrodes 16b at the respective distal and proximal ends of the balloon of the balloon catheter 1 have been described as being equi-spaced of minimum axially spacing, many more than three such minimum axially spaced apart sensing electrodes may be provided. It will of course be appreciated that more than one sensing electrode of progressively decreasing spacing between each other may be provided between the sensing electrodes 16a and the sensing electrodes 16b. Indeed, in certain cases it is envisaged that only two sensing electrodes of maximum axial spacing may be provided, and in which case, the sensing electrodes would be of progressively decreasing axial spacing from the two sensing electrodes of maximum axial spacing. It is also envisaged that the spacing of the sensing electrodes from the sensing electrodes of maximum axial spacing may progressively decrease to a single pair of sensing electrodes which would be of minimum axial spacing.

Similarly, it will be appreciated that the number of sensing electrodes 16a and the number of sensing electrodes 16b of the balloon catheters 60, 65 and 70 will be dependent on the axial lengths of the central portion of the balloon and the proximal and distal end portions of the balloon.

It is also envisaged that while the sensing electrodes of maximum axial spacing have been described as being located centrally in the balloon, the sensing electrodes of maximum axial spacing will be located adjacent the portion of the balloon of greatest transverse cross-sectional area. Where the portions of the balloon of greatest transverse cross-sectional area are located towards the proximal and/or distal ends of the balloon, the spacing between the sensing electrodes towards the proximal and/or distal ends of the greatest transverse cross-sectional area will be greater than the spacing between the sensing electrodes adjacent the central portion of the balloon or the other of the proximal and distal portions, which will be of least transverse cross-sectional area, as in the case of the balloon catheter. Where located towards both the proximal and distal ends of the balloon, it is envisaged that the spacing between the sensing electrodes may progressively decrease to the sensing electrodes located adjacent the central portion of the balloon, as in the case of the balloon catheter 65. Such an arrangement of sensing electrodes would be particularly suitable for determining the transverse cross-sectional area of a sphincter or a vessel with an axial central necked portion as has already been described.

It is also envisaged that where the sensing electrodes of maximum spacing are located towards either the proximal or distal ends of the balloon, the axial spacing between the sensing electrodes may progressively decrease towards the other of the proximal and distal end of the balloon.

While the stimulating and sensing electrodes of the various balloon catheters described herein have been described as being of band type electrodes, any other suitable stimulating and sensing electrodes may be provided.

While the balloon catheters 75, 85, 95, 100, 105 and 110 have been described as comprising a single guide wire engaging element, and in particular, while the balloon catheters have been described as comprising a guide wire engaging element adjacent the distal end of the catheter, while it is preferable to provide the guide wire engaging element as close as possible to the distal end of the catheter, in certain cases, it is envisaged that the guide wire engaging element may be provided spaced apart in a proximal direction from the distal end of the catheter. Indeed, it is envisaged in certain cases that the balloon catheters may be provided with a plurality of guide wire engaging elements at spaced apart locations along the balloon catheter. The plurality of guide wire engaging elements may be located towards the distal end of the balloon catheter, or may be provided along the entire length of the balloon catheter. It is also envisaged that instead of providing one or a plurality of guide wire engaging elements, a single guide wire engaging element may be provided by an elongated lumen extending along the exterior of the catheter for accommodating a guide wire therethrough. Such an elongated lumen would be dedicated to accommodating a guide wire.

While the catheters 75, 85, 95, 100, 105 and 110 have been described as being balloon catheters, it is envisaged that the catheters may be any type of catheter, whether balloon catheters or otherwise.

Although not illustrated, it is envisaged that the catheters 1, 60, 65 and 70 may be provided with an additional lumen extending through the catheter from the proximal end to the distal end for accommodating a guide wire.

While the catheters according to the invention have been described for use in carrying out a procedure or investigation at a remote site in a human or animal subject, the remote site may be any type of site, be it in the digestive system, the cardiovascular system, the vascular system generally, the urinary tract system, in the reproductive organs of the male or female, or any other remote site in the body of a human or animal subject which is accessible orally, nasally, rectally, through the penis, vagina, urethra, or through the vascular or cardiovascular system of the body of a human or animal subject.

It is also envisaged that in certain cases, the balloon catheters may be provided without measuring electrodes, and where the balloon catheters are provided with measuring electrodes, it is envisaged that in some cases two measuring electrodes may be sufficient.

While the balloon catheters and the apparatus have been described for carrying out a specific procedure, it will be readily apparent to those skilled in the art that the apparatus and the balloon catheter may be used for any other procedures or investigations.

It is also envisaged that other suitable graphical representations of the balloon of the balloon catheter may be displayed on the visual display screen of the visual display unit, for example, the graphical representation of the balloon instead of being a two-dimensional representation, may be a three-dimensional representation. Where the graphical representation of the balloon is displayed as a three-dimensional representation, it is envisaged that it would be assumed that the balloon would take up a shape of circular transverse cross-section.

While the means for determining the tightness to which the gastric band has been tightened around the stomach to form the stoma in the embodiment of the invention described with reference to FIG. 24 has been described as being a function of the volume of inflating medium in the inflatable cuff, it is envisaged in certain cases, the tightness to which the gastric band has been tightened around the stomach may be determined as a function of the pressure of the inflating medium in the inflatable cuff of the gastric band, and in which case, it is envisaged that a pressure monitoring means would be provided for monitoring the pressure of the inflating medium in the inflatable cuff of the gastric band.

While the inflating medium for inflating the balloon of the balloon catheter has been described as being a saline solution, any suitable inflating medium may be used, and where the balloon catheter includes measuring means provided by stimulating and sensing electrodes, the inflating medium would be an electrically conductive inflating medium. The medium may be in liquid or gaseous form.

Additionally, it will be appreciated that any suitable inflating medium, whether gaseous or liquid, may be used for inflating the inflatable cuff of the gastric band. Needless to say, there is no requirement for the inflating medium for the inflatable cuff of the gastric band to be an electrically conductive medium, although, in general, a liquid inflating medium is preferable to a gaseous medium, and a saline solution is a suitable inflating medium.

While the balloon catheter for use in the monitoring and formation of a stoma in a stomach has been described as not completely filling the stomach, it is envisaged in many cases, the balloon of the balloon catheter may be sized to fill the entire stomach, and in which case, the distal end of the balloon catheter, and in turn the distal end of the balloon would be engaged in the pylorus of the stomach.

It is also envisaged that other suitable means for detecting the tightness of the gastric band around the stomach may be used besides monitoring the inflating medium in the inflatable cuff, for example, strain gauges, pressure gauges and the like.

It will also be appreciated that instead of monitoring the volume of inflating medium in the inflatable cuff of the gastric band in order to determine the tightness of the gastric band around the stomach, it is envisaged that the tightness of the gastric band may be determined by monitoring the pressure of the inflating medium in the inflatable cuff of the gastric band.

The invention claimed is:

1. A balloon catheter comprising:
an elongated catheter extending between a proximal end and a distal end,
an inflatable element defining a hollow interior region located on the catheter,
a first lumen extending along the catheter from the proximal end to the inflatable element communicating with the inflatable element for accommodating an inflating medium to the inflatable element,
a non-deformable elongated tubular protective housing having a chamber formed therein located within a cavity formed in the catheter adjacent the inflatable element, the cavity in the catheter communicating with the hollow interior region of the inflatable element, the protective housing terminating at one end in a communicating opening, the communicating opening communicating the chamber of the protective housing with the hollow interior region of the inflatable element,
a pressure sensing element located in the chamber of the protective housing and being free floating therein and communicating with the hollow interior region of the inflatable element through the communicating opening in the protective housing and the cavity in the catheter for sensing pressure of an inflating medium in the inflatable element.

2. A balloon catheter as claimed in claim 1 in which the protective housing is of circular transverse cross-section.

3. A balloon catheter as claimed in claim 1 in which the pressure sensing element comprises a solid state strain gauge.

4. A balloon catheter as claimed in claim 1 in which the catheter extends through the inflatable element, and the inflatable element defines with the catheter the hollow interior region as an annular hollow interior region.

5. A balloon catheter as claimed in claim 1 in which a tubular port extends from the protective housing, the tubular port being adapted for accommodating at least one electrically conductive wire to the pressure sensing element.

6. A balloon catheter as claimed in claim 5 in which the tubular port forms the communicating opening.

7. A balloon catheter as claimed in claim 5 in which the tubular port extends from the protective housing at an end opposite to the end which terminates in the communicating opening.

8. A balloon catheter as claimed in claim 5 in which the at least one electrically conductive wire is secured to the protective housing.

9. A balloon catheter as claimed in claim 5 in which the at least one electrically conductive wire is secured to the protective housing by an adhesive.

10. A balloon catheter as claimed in claim 5 in which the at least one electrically conductive wire extends to the pressure sensing element from the proximal end of the catheter.

11. A balloon catheter as claimed in claim 1 in which the inflatable element is located on the catheter adjacent the distal end thereof.

12. A balloon catheter as claimed in claim 1 in which a measuring means is provided for determining a transverse cross-sectional dimension of the inflatable element, the measuring means comprising a pair of axially spaced apart stimulating electrodes located within the inflatable element on one of the catheter and the inflatable element for receiving an electrical stimulating signal, and a plurality of axially spaced apart sensing electrodes located within the inflatable element on one of the catheter and the inflatable element, the sensing electrodes being located between the stimulating electrodes and axially spaced apart therefrom and being responsive to a stimulating signal applied to the stimulating electrodes when the inflatable element is inflated with an electrically conductive medium for producing a response signal indicative of a value of the transverse cross-sectional dimension of the inflatable element adjacent the corresponding sensing electrode.

13. A balloon catheter as claimed in claim 12 in which the axial spacing between at least two of the sensing electrodes is greater than the axial spacing between others of the sensing electrodes.

14. A balloon catheter as claimed in claim 13 in which the greatest axial spacing between the sensing electrodes lies in the range of 5 mm to 10 mm, and the minimum axial spacing between the sensing electrodes lies in the range of 2 mm to 5 mm.

15. A balloon catheter as claimed in claim 13 in which the axial spacing between the sensing electrodes is greatest at a location where the transverse cross-section of the inflatable element is adapted to be greatest.

16. A balloon catheter as claimed in claim 13 in which the axial spacing between the sensing electrodes progressively decreases from the sensing electrodes of greatest axial spacing therebetween to the sensing electrodes of least axial spacing therebetween.

* * * * *